US012630872B1

(12) United States Patent
Le et al.

(10) Patent No.: US 12,630,872 B1
(45) Date of Patent: May 19, 2026

(54) METHOD FOR DETECTING A TARGETED NUCLEIC ACID FROM A DEOXYRIBONUCLEIC ACID (DNA) SAMPLE EXTRACTED USING A DNA EXTRACTION KIT THROUGH DNA AMPLIFICATION TESTING

(71) Applicant: Truc Linh Thi Le, Lam Dong (VN)

(72) Inventors: Truc Linh Thi Le, Lam Dong (VN); Ai Thuy Huyen Le, Ho Chi Minh (VN); Thuan Duc Lao, Ho Chi Minh (VN); Nguyen Hoai Nguyen, Tay Ninh (VN); Uyen Phuong Le, Khanh Hoa (VN)

(73) Assignee: Biosci RD Corporation, Irvine, CA (US)

( * ) Notice: Subject to any disclaimer, the term of this patent is extended or adjusted under 35 U.S.C. 154(b) by 0 days.

(21) Appl. No.: 19/284,713

(22) Filed: Jul. 30, 2025

(51) Int. Cl.
　　*C12Q 1/68*　　　　(2018.01)
　　*C12Q 1/6806*　　　(2018.01)
　　*C12Q 1/6851*　　　(2018.01)
　　*C12Q 1/70*　　　　(2006.01)

(52) U.S. Cl.
　　CPC ......... *C12Q 1/6851* (2013.01); *C12Q 1/6806* (2013.01); *C12Q 1/701* (2013.01)

(58) Field of Classification Search
None
See application file for complete search history.

(56) References Cited

FOREIGN PATENT DOCUMENTS

WO　　WO-2018195594 A1 * 11/2018　......... C12N 15/1006

* cited by examiner

*Primary Examiner* — Aaron A Priest

(57) ABSTRACT

A method for detecting a targeted nucleic acid from a deoxyribonucleic acid (DNA) sample extracted using a DNA extraction kit through DNA amplification testing comprising: (i) preparing a DNA extraction kit and a test sample; (ii) adding the test sample to the tube containing the lysis buffer, shaking and incubating to obtain a sample-containing tube; (iii) shaking the sample-containing tube, then immersing the dipstick into the sample-containing tube to obtain a sample-loaded dipstick; (iv) transferring the sample-loaded dipstick into the tube containing the wash buffer, removing excess wash buffer from the dipstick to obtain a dipstick containing the DNA from the test sample; and (v) amplifying the DNA from the dipstick containing the DNA of the test sample using a DNA amplification technique and reading the result to detect the targeted nucleic acid.

20 Claims, 18 Drawing Sheets

Specification includes a Sequence Listing.

50 mm ─── A handle portion 3 mm ─── A fluid-barrier portion 3 mm ─── A nucleic acid-capture portion 2 mm 50 mm ----- A handle portion 3 mm ----- A fluid-barrier portion 3 mm ----- A nucleic acid-capture portion 2 mm Negative control Negative control Negative control Negative control Negative control Negative control

SEQUENCE LISTING

Sequence total quantity: 118
SEQ ID NO: 1          moltype = DNA  length = 22
FEATURE               Location/Qualifiers
source                1..22

```
                        mol_type = other DNA
                        organism = synthetic construct
SEQUENCE: 1
ccatcaaagt tctgcagctc tt                                                    22

SEQ ID NO: 2            moltype = DNA   length = 21
FEATURE                 Location/Qualifiers
source                  1..21
                        mol_type = other DNA
                        organism = synthetic construct
SEQUENCE: 2
cacaagatca gccgtagtga t                                                     21

SEQ ID NO: 3            moltype = DNA   length = 21
FEATURE                 Location/Qualifiers
source                  1..21
                        mol_type = other DNA
                        organism = synthetic construct
SEQUENCE: 3
cacaagatca gccgtggtga t                                                     21

SEQ ID NO: 4            moltype = DNA   length = 21
FEATURE                 Location/Qualifiers
source                  1..21
                        mol_type = other DNA
                        organism = synthetic construct
SEQUENCE: 4
cacaagatcg gccgtagtga t                                                     21

SEQ ID NO: 5            moltype = DNA   length = 21
FEATURE                 Location/Qualifiers
source                  1..21
                        mol_type = other DNA
                        organism = synthetic construct
SEQUENCE: 5
cacaagatcg gccgtggtga t                                                     21

SEQ ID NO: 6            moltype = DNA   length = 42
FEATURE                 Location/Qualifiers
source                  1..42
                        mol_type = other DNA
                        organism = synthetic construct
SEQUENCE: 6
gcaaaggtaa tcatcatcgc acccaccctt ccactacgga gg                             42

SEQ ID NO: 7            moltype = DNA   length = 42
FEATURE                 Location/Qualifiers
source                  1..42
                        mol_type = other DNA
                        organism = synthetic construct
SEQUENCE: 7
gcaaaggtaa tcatcatcgc acccaccctt ccactatgga gg                             42

SEQ ID NO: 8            moltype = DNA   length = 42
FEATURE                 Location/Qualifiers
source                  1..42
                        mol_type = other DNA
                        organism = synthetic construct
SEQUENCE: 8
gcaaaggtaa tcatcatcgc acccaccctt tcactacgga gg                             42

SEQ ID NO: 9            moltype = DNA   length = 42
FEATURE                 Location/Qualifiers
source                  1..42
                        mol_type = other DNA
                        organism = synthetic construct
SEQUENCE: 9
gcaaaggtaa tcatcatcgc acccaccctt tcactatgga gg                             42

SEQ ID NO: 10           moltype = DNA   length = 42
FEATURE                 Location/Qualifiers
source                  1..42
                        mol_type = other DNA
                        organism = synthetic construct
SEQUENCE: 10
gcaaaggtaa tcatcatcgc gcccaccctt ccactacgga gg                             42

SEQ ID NO: 11           moltype = DNA   length = 42
FEATURE                 Location/Qualifiers
```

-continued

```
source                  1..42
                        mol_type = other DNA
                        organism = synthetic construct
SEQUENCE: 11
gcaaaggtaa tcatcatcgc gcccacccct ccactatgga gg                          42

SEQ ID NO: 12           moltype = DNA   length = 42
FEATURE                 Location/Qualifiers
source                  1..42
                        mol_type = other DNA
                        organism = synthetic construct
SEQUENCE: 12
gcaaaggtaa tcatcatcgc gcccacccct tcactacgga gg                          42

SEQ ID NO: 13           moltype = DNA   length = 42
FEATURE                 Location/Qualifiers
source                  1..42
                        mol_type = other DNA
                        organism = synthetic construct
SEQUENCE: 13
gcaaaggtaa tcatcatcgc gcccacccct tcactatgga gg                          42

SEQ ID NO: 14           moltype = DNA   length = 42
FEATURE                 Location/Qualifiers
source                  1..42
                        mol_type = other DNA
                        organism = synthetic construct
SEQUENCE: 14
gcgaaggtaa tcatcatcgc acccacccct ccactacgga gg                          42

SEQ ID NO: 15           moltype = DNA   length = 42
FEATURE                 Location/Qualifiers
source                  1..42
                        mol_type = other DNA
                        organism = synthetic construct
SEQUENCE: 15
gcgaaggtaa tcatcatcgc acccacccct ccactatgga gg                          42

SEQ ID NO: 16           moltype = DNA   length = 42
FEATURE                 Location/Qualifiers
source                  1..42
                        mol_type = other DNA
                        organism = synthetic construct
SEQUENCE: 16
gcgaaggtaa tcatcatcgc acccacccct tcactacgga gg                          42

SEQ ID NO: 17           moltype = DNA   length = 42
FEATURE                 Location/Qualifiers
source                  1..42
                        mol_type = other DNA
                        organism = synthetic construct
SEQUENCE: 17
gcgaaggtaa tcatcatcgc acccacccct tcactatgga gg                          42

SEQ ID NO: 18           moltype = DNA   length = 42
FEATURE                 Location/Qualifiers
source                  1..42
                        mol_type = other DNA
                        organism = synthetic construct
SEQUENCE: 18
gcgaaggtaa tcatcatcgc gcccacccct tcactacgga gg                          42

SEQ ID NO: 19           moltype = DNA   length = 42
FEATURE                 Location/Qualifiers
source                  1..42
                        mol_type = other DNA
                        organism = synthetic construct
SEQUENCE: 19
gcgaaggtaa tcatcatcgc gcccacccct ccactatgga gg                          42

SEQ ID NO: 20           moltype = DNA   length = 42
FEATURE                 Location/Qualifiers
source                  1..42
                        mol_type = other DNA
                        organism = synthetic construct
SEQUENCE: 20
gcgaaggtaa tcatcatcgc gcccacccct tcactacgga gg                          42

SEQ ID NO: 21           moltype = DNA   length = 42
```

-continued

```
FEATURE                 Location/Qualifiers
source                  1..42
                        mol_type = other DNA
                        organism = synthetic construct
SEQUENCE: 21
gcgaaggtaa tcatcatcgc gcccaccctt tcactatgga gg                          42

SEQ ID NO: 22           moltype = DNA   length = 43
FEATURE                 Location/Qualifiers
source                  1..43
                        mol_type = other DNA
                        organism = synthetic construct
SEQUENCE: 22
ggaggaatac caacccagcg gcctcccaca taatccgtat ccc                         43

SEQ ID NO: 23           moltype = DNA   length = 43
FEATURE                 Location/Qualifiers
source                  1..43
                        mol_type = other DNA
                        organism = synthetic construct
SEQUENCE: 23
ggaggaatac caacccagcg gcctcccaca taatccgtgt ccc                         43

SEQ ID NO: 24           moltype = DNA   length = 43
FEATURE                 Location/Qualifiers
source                  1..43
                        mol_type = other DNA
                        organism = synthetic construct
SEQUENCE: 24
ggaggaatac caacccagcg gcctcccaca taatctgtat ccc                         43

SEQ ID NO: 25           moltype = DNA   length = 43
FEATURE                 Location/Qualifiers
source                  1..43
                        mol_type = other DNA
                        organism = synthetic construct
SEQUENCE: 25
ggaggaatac caacccagcg gcctcccaca taatctgtgt ccc                         43

SEQ ID NO: 26           moltype = DNA   length = 43
FEATURE                 Location/Qualifiers
source                  1..43
                        mol_type = other DNA
                        organism = synthetic construct
SEQUENCE: 26
ggaggaatac caacccagcg gcctcccacg taatccgtat ccc                         43

SEQ ID NO: 27           moltype = DNA   length = 43
FEATURE                 Location/Qualifiers
source                  1..43
                        mol_type = other DNA
                        organism = synthetic construct
SEQUENCE: 27
ggaggaatac caacccagcg gcctcccacg taatccgtgt ccc                         43

SEQ ID NO: 28           moltype = DNA   length = 43
FEATURE                 Location/Qualifiers
source                  1..43
                        mol_type = other DNA
                        organism = synthetic construct
SEQUENCE: 28
ggaggaatac caacccagcg gcctcccacg taatctgtat ccc                         43

SEQ ID NO: 29           moltype = DNA   length = 43
FEATURE                 Location/Qualifiers
source                  1..43
                        mol_type = other DNA
                        organism = synthetic construct
SEQUENCE: 29
ggaggaatac caacccagcg gcctcccacg taatctgtgt ccc                         43

SEQ ID NO: 30           moltype = DNA   length = 43
FEATURE                 Location/Qualifiers
source                  1..43
                        mol_type = other DNA
                        organism = synthetic construct
SEQUENCE: 30
ggaggaatac caacccagcg gtctcccaca taatccgtat ccc                         43
```

-continued

```
SEQ ID NO: 31          moltype = DNA  length = 43
FEATURE                Location/Qualifiers
source                 1..43
                       mol_type = other DNA
                       organism = synthetic construct
SEQUENCE: 31
ggaggaatac caacccagcg gtctcccaca taatccgtgt ccc                        43

SEQ ID NO: 32          moltype = DNA  length = 43
FEATURE                Location/Qualifiers
source                 1..43
                       mol_type = other DNA
                       organism = synthetic construct
SEQUENCE: 32
ggaggaatac caacccagcg gtctcccaca taatctgtat ccc                        43

SEQ ID NO: 33          moltype = DNA  length = 43
FEATURE                Location/Qualifiers
source                 1..43
                       mol_type = other DNA
                       organism = synthetic construct
SEQUENCE: 33
ggaggaatac caacccagcg gtctcccaca taatctgtgt ccc                        43

SEQ ID NO: 34          moltype = DNA  length = 43
FEATURE                Location/Qualifiers
source                 1..43
                       mol_type = other DNA
                       organism = synthetic construct
SEQUENCE: 34
ggaggaatac caacccagcg gtctcccacg taatccgtat ccc                        43

SEQ ID NO: 35          moltype = DNA  length = 43
FEATURE                Location/Qualifiers
source                 1..43
                       mol_type = other DNA
                       organism = synthetic construct
SEQUENCE: 35
ggaggaatac caacccagcg gtctcccacg taatccgtgt ccc                        43

SEQ ID NO: 36          moltype = DNA  length = 43
FEATURE                Location/Qualifiers
source                 1..43
                       mol_type = other DNA
                       organism = synthetic construct
SEQUENCE: 36
ggaggaatac caacccagcg gtctcccacg taatctgtat ccc                        43

SEQ ID NO: 37          moltype = DNA  length = 43
FEATURE                Location/Qualifiers
source                 1..43
                       mol_type = other DNA
                       organism = synthetic construct
SEQUENCE: 37
ggaggaatac caacccagcg gtctcccacg taatctgtgt ccc                        43

SEQ ID NO: 38          moltype = DNA  length = 43
FEATURE                Location/Qualifiers
source                 1..43
                       mol_type = other DNA
                       organism = synthetic construct
SEQUENCE: 38
ggaggaatac caacccagtg gcctcccaca taatccgtat ccc                        43

SEQ ID NO: 39          moltype = DNA  length = 43
FEATURE                Location/Qualifiers
source                 1..43
                       mol_type = other DNA
                       organism = synthetic construct
SEQUENCE: 39
ggaggaatac caacccagtg gcctcccaca taatccgtgt ccc                        43

SEQ ID NO: 40          moltype = DNA  length = 43
FEATURE                Location/Qualifiers
source                 1..43
                       mol_type = other DNA
                       organism = synthetic construct
SEQUENCE: 40
ggaggaatac caacccagtg gcctcccaca taatctgtat ccc                        43
```

```
SEQ ID NO: 41              moltype = DNA   length = 43
FEATURE                    Location/Qualifiers
source                     1..43
                           mol_type = other DNA
                           organism = synthetic construct
SEQUENCE: 41
ggaggaatac caacccagtg gcctcccaca taatctgtgt ccc                         43

SEQ ID NO: 42              moltype = DNA   length = 43
FEATURE                    Location/Qualifiers
source                     1..43
                           mol_type = other DNA
                           organism = synthetic construct
SEQUENCE: 42
ggaggaatac caacccagtg gcctcccacg taatccgtat ccc                         43

SEQ ID NO: 43              moltype = DNA   length = 43
FEATURE                    Location/Qualifiers
source                     1..43
                           mol_type = other DNA
                           organism = synthetic construct
SEQUENCE: 43
ggaggaatac caacccagtg gcctcccacg taatctgtat ccc                         43

SEQ ID NO: 44              moltype = DNA   length = 43
FEATURE                    Location/Qualifiers
source                     1..43
                           mol_type = other DNA
                           organism = synthetic construct
SEQUENCE: 44
ggaggaatac caacccagtg gcctcccacg taatctgtat ccc                         43

SEQ ID NO: 45              moltype = DNA   length = 43
FEATURE                    Location/Qualifiers
source                     1..43
                           mol_type = other DNA
                           organism = synthetic construct
SEQUENCE: 45
ggaggaatac caacccagtg gcctcccacg taatctgtgt ccc                         43

SEQ ID NO: 46              moltype = DNA   length = 43
FEATURE                    Location/Qualifiers
source                     1..43
                           mol_type = other DNA
                           organism = synthetic construct
SEQUENCE: 46
ggaggaatac caacccagtg gtctcccaca taatccgtat ccc                         43

SEQ ID NO: 47              moltype = DNA   length = 43
FEATURE                    Location/Qualifiers
source                     1..43
                           mol_type = other DNA
                           organism = synthetic construct
SEQUENCE: 47
ggaggaatac caacccagtg gtctcccaca taatccgtgt ccc                         43

SEQ ID NO: 48              moltype = DNA   length = 43
FEATURE                    Location/Qualifiers
source                     1..43
                           mol_type = other DNA
                           organism = synthetic construct
SEQUENCE: 48
ggaggaatac caacccagtg gtctcccaca taatctgtat ccc                         43

SEQ ID NO: 49              moltype = DNA   length = 43
FEATURE                    Location/Qualifiers
source                     1..43
                           mol_type = other DNA
                           organism = synthetic construct
SEQUENCE: 49
ggaggaatac caacccagtg gtctcccaca taatctgtgt ccc                         43

SEQ ID NO: 50              moltype = DNA   length = 43
FEATURE                    Location/Qualifiers
source                     1..43
                           mol_type = other DNA
                           organism = synthetic construct
SEQUENCE: 50
```

```
ggaggaatac caacccagtg gtctcccacg taatccgtat ccc                            43

SEQ ID NO: 51            moltype = DNA   length = 43
FEATURE                  Location/Qualifiers
source                   1..43
                         mol_type = other DNA
                         organism = synthetic construct
SEQUENCE: 51
ggaggaatac caacccagtg gtctcccacg taatccgtgt ccc                            43

SEQ ID NO: 52            moltype = DNA   length = 43
FEATURE                  Location/Qualifiers
source                   1..43
                         mol_type = other DNA
                         organism = synthetic construct
SEQUENCE: 52
ggaggaatac caacccagtg gtctcccacg taatctgtat ccc                            43

SEQ ID NO: 53            moltype = DNA   length = 43
FEATURE                  Location/Qualifiers
source                   1..43
                         mol_type = other DNA
                         organism = synthetic construct
SEQUENCE: 53
ggaggaatac caacccagtg gtctcccacg taatctgtgt ccc                            43

SEQ ID NO: 54            moltype = DNA   length = 18
FEATURE                  Location/Qualifiers
source                   1..18
                         mol_type = other DNA
                         organism = synthetic construct
SEQUENCE: 54
ccaggatcat caggagtt                                                        18

SEQ ID NO: 55            moltype = DNA   length = 18
FEATURE                  Location/Qualifiers
source                   1..18
                         mol_type = other DNA
                         organism = synthetic construct
SEQUENCE: 55
ccaggatcat caggggtt                                                        18

SEQ ID NO: 56            moltype = DNA   length = 18
FEATURE                  Location/Qualifiers
source                   1..18
                         mol_type = other DNA
                         organism = synthetic construct
SEQUENCE: 56
ccaggatcat cgggagtt                                                        18

SEQ ID NO: 57            moltype = DNA   length = 18
FEATURE                  Location/Qualifiers
source                   1..18
                         mol_type = other DNA
                         organism = synthetic construct
SEQUENCE: 57
ccaggatcat cgggggtt                                                        18

SEQ ID NO: 58            moltype = DNA   length = 18
FEATURE                  Location/Qualifiers
source                   1..18
                         mol_type = other DNA
                         organism = synthetic construct
SEQUENCE: 58
ccaggatcgt caggagtt                                                        18

SEQ ID NO: 59            moltype = DNA   length = 18
FEATURE                  Location/Qualifiers
source                   1..18
                         mol_type = other DNA
                         organism = synthetic construct
SEQUENCE: 59
ccaggatcgt caggggtt                                                        18

SEQ ID NO: 60            moltype = DNA   length = 18
FEATURE                  Location/Qualifiers
source                   1..18
                         mol_type = other DNA
                         organism = synthetic construct
```

-continued

```
SEQUENCE: 60
ccaggatcgt cgggagtt                                              18

SEQ ID NO: 61          moltype = DNA  length = 18
FEATURE                Location/Qualifiers
source                 1..18
                       mol_type = other DNA
                       organism = synthetic construct
SEQUENCE: 61
ccaggatcgt cggggtt                                               18

SEQ ID NO: 62          moltype = DNA  length = 18
FEATURE                Location/Qualifiers
source                 1..18
                       mol_type = other DNA
                       organism = synthetic construct
SEQUENCE: 62
cccggatcat caggagtt                                              18

SEQ ID NO: 63          moltype = DNA  length = 18
FEATURE                Location/Qualifiers
source                 1..18
                       mol_type = other DNA
                       organism = synthetic construct
SEQUENCE: 63
cccggatcat caggggtt                                              18

SEQ ID NO: 64          moltype = DNA  length = 18
FEATURE                Location/Qualifiers
source                 1..18
                       mol_type = other DNA
                       organism = synthetic construct
SEQUENCE: 64
cccggatcat cgggagtt                                              18

SEQ ID NO: 65          moltype = DNA  length = 18
FEATURE                Location/Qualifiers
source                 1..18
                       mol_type = other DNA
                       organism = synthetic construct
SEQUENCE: 65
cccggatcat cggggtt                                               18

SEQ ID NO: 66          moltype = DNA  length = 18
FEATURE                Location/Qualifiers
source                 1..18
                       mol_type = other DNA
                       organism = synthetic construct
SEQUENCE: 66
cccggatcgt caggagtt                                              18

SEQ ID NO: 67          moltype = DNA  length = 18
FEATURE                Location/Qualifiers
source                 1..18
                       mol_type = other DNA
                       organism = synthetic construct
SEQUENCE: 67
cccggatcgt caggggtt                                              18

SEQ ID NO: 68          moltype = DNA  length = 18
FEATURE                Location/Qualifiers
source                 1..18
                       mol_type = other DNA
                       organism = synthetic construct
SEQUENCE: 68
cccggatcgt cgggagtt                                              18

SEQ ID NO: 69          moltype = DNA  length = 18
FEATURE                Location/Qualifiers
source                 1..18
                       mol_type = other DNA
                       organism = synthetic construct
SEQUENCE: 69
cccggatcgt cggggtt                                               18

SEQ ID NO: 70          moltype = DNA  length = 25
FEATURE                Location/Qualifiers
source                 1..25
                       mol_type = other DNA
```

-continued

```
                          organism = synthetic construct
SEQUENCE: 70
gccatattaa cgtatccaga gcaag                                                25

SEQ ID NO: 71             moltype = DNA   length = 25
FEATURE                   Location/Qualifiers
source                    1..25
                          mol_type = other DNA
                          organism = synthetic construct
SEQUENCE: 71
gccatattaa cgtatctaga gcaag                                                25

SEQ ID NO: 72             moltype = DNA   length = 25
FEATURE                   Location/Qualifiers
source                    1..25
                          mol_type = other DNA
                          organism = synthetic construct
SEQUENCE: 72
gccatattaa tgtatccaga gcaag                                                25

SEQ ID NO: 73             moltype = DNA   length = 25
FEATURE                   Location/Qualifiers
source                    1..25
                          mol_type = other DNA
                          organism = synthetic construct
SEQUENCE: 73
gccatattaa tgtatctaga gcaag                                                25

SEQ ID NO: 74             moltype = DNA   length = 25
FEATURE                   Location/Qualifiers
source                    1..25
                          mol_type = other DNA
                          organism = synthetic construct
SEQUENCE: 74
gtcatattaa cgtatccaga gcaag                                                25

SEQ ID NO: 75             moltype = DNA   length = 25
FEATURE                   Location/Qualifiers
source                    1..25
                          mol_type = other DNA
                          organism = synthetic construct
SEQUENCE: 75
gtcatattaa cgtatctaga gcaag                                                25

SEQ ID NO: 76             moltype = DNA   length = 25
FEATURE                   Location/Qualifiers
source                    1..25
                          mol_type = other DNA
                          organism = synthetic construct
SEQUENCE: 76
gtcatattaa tgtatccaga gcaag                                                25

SEQ ID NO: 77             moltype = DNA   length = 25
FEATURE                   Location/Qualifiers
source                    1..25
                          mol_type = other DNA
                          organism = synthetic construct
SEQUENCE: 77
gtcatattaa tgtatctaga gcaag                                                25

SEQ ID NO: 78             moltype = DNA   length = 20
FEATURE                   Location/Qualifiers
source                    1..20
                          mol_type = other DNA
                          organism = synthetic construct
SEQUENCE: 78
agttatggga aacccgaccc                                                      20

SEQ ID NO: 79             moltype = DNA   length = 19
FEATURE                   Location/Qualifiers
source                    1..19
                          mol_type = other DNA
                          organism = synthetic construct
SEQUENCE: 79
ccctgaatcg gagcatcct                                                       19

SEQ ID NO: 80             moltype = DNA   length = 25
FEATURE                   Location/Qualifiers
source                    1..25
```

```
                        mol_type = other DNA
                        organism = synthetic construct
SEQUENCE: 80
ctgctcatgg tatcaatctt atcga                                     25

SEQ ID NO: 81          moltype = DNA   length = 21
FEATURE                Location/Qualifiers
source                 1..21
                        mol_type = other DNA
                        organism = synthetic construct
SEQUENCE: 81
gataccacaa gatcagccgt a                                         21

SEQ ID NO: 82          moltype = DNA   length = 19
FEATURE                Location/Qualifiers
source                 1..19
                        mol_type = other DNA
                        organism = synthetic construct
SEQUENCE: 82
ctcggtgttg atgaggatt                                            19

SEQ ID NO: 83          moltype = DNA   length = 19
FEATURE                Location/Qualifiers
source                 1..19
                        mol_type = other DNA
                        organism = synthetic construct
SEQUENCE: 83
cccctgaaat acacaacct                                            19

SEQ ID NO: 84          moltype = DNA   length = 44
FEATURE                Location/Qualifiers
source                 1..44
                        mol_type = other DNA
                        organism = synthetic construct
SEQUENCE: 84
tgctcttaaa tggcccattg aatattgatc ggagatgttc cagg               44

SEQ ID NO: 85          moltype = DNA   length = 41
FEATURE                Location/Qualifiers
source                 1..41
                        mol_type = other DNA
                        organism = synthetic construct
SEQUENCE: 85
tcatcgtggt ggttattgtt ggttttgtaa aacgcgttcg c                  41

SEQ ID NO: 86          moltype = DNA   length = 20
FEATURE                Location/Qualifiers
source                 1..20
                        mol_type = other DNA
                        organism = synthetic construct
SEQUENCE: 86
tgtttatagg attaaaacct                                           20

SEQ ID NO: 87          moltype = DNA   length = 23
FEATURE                Location/Qualifiers
source                 1..23
                        mol_type = other DNA
                        organism = synthetic construct
SEQUENCE: 87
gtcacctgcg ttttatggac acg                                       23

SEQ ID NO: 88          moltype = DNA   length = 18
FEATURE                Location/Qualifiers
source                 1..18
                        mol_type = other DNA
                        organism = synthetic construct
SEQUENCE: 88
atcctgcgtc tggacctg                                             18

SEQ ID NO: 89          moltype = DNA   length = 18
FEATURE                Location/Qualifiers
source                 1..18
                        mol_type = other DNA
                        organism = synthetic construct
SEQUENCE: 89
tctccaggga ggaggagg                                             18

SEQ ID NO: 90          moltype = DNA   length = 40
FEATURE                Location/Qualifiers
```

```
source                    1..40
                          mol_type = other DNA
                          organism = synthetic construct
SEQUENCE: 90
cgtggtggtg aagctgtagc ctgggacctg accgactacc                              40

SEQ ID NO: 91             moltype = DNA   length = 40
FEATURE                   Location/Qualifiers
source                    1..40
                          mol_type = other DNA
                          organism = synthetic construct
SEQUENCE: 91
cgggagatcg tgcgggacat ccatctcctg ctcgaagtcc                              40

SEQ ID NO: 92             moltype = DNA   length = 21
FEATURE                   Location/Qualifiers
source                    1..21
                          mol_type = other DNA
                          organism = synthetic construct
SEQUENCE: 92
cgctccgtga ggatcttcat g                                                  21

SEQ ID NO: 93             moltype = DNA   length = 21
FEATURE                   Location/Qualifiers
source                    1..21
                          mol_type = other DNA
                          organism = synthetic construct
SEQUENCE: 93
cgctccgtca ggatcttcat g                                                  21

SEQ ID NO: 94             moltype = DNA   length = 23
FEATURE                   Location/Qualifiers
source                    1..23
                          mol_type = other DNA
                          organism = synthetic construct
SEQUENCE: 94
caaggagaag ctgtgctacg tcg                                                23

SEQ ID NO: 95             moltype = DNA   length = 21
FEATURE                   Location/Qualifiers
source                    1..21
                          mol_type = other DNA
                          organism = synthetic construct
SEQUENCE: 95
cgctccgtca ggatcttcat g                                                  21

SEQ ID NO: 96             moltype = DNA   length = 20
FEATURE                   Location/Qualifiers
source                    1..20
                          mol_type = other DNA
                          organism = synthetic construct
SEQUENCE: 96
ttgcaactgt aatggctatg                                                    20

SEQ ID NO: 97             moltype = DNA   length = 21
FEATURE                   Location/Qualifiers
source                    1..21
                          mol_type = other DNA
                          organism = synthetic construct
SEQUENCE: 97
cgcagttcct aatttaccat g                                                  21

SEQ ID NO: 98             moltype = DNA   length = 43
FEATURE                   Location/Qualifiers
source                    1..43
                          mol_type = other DNA
                          organism = synthetic construct
SEQUENCE: 98
ttgctttcac attttggctg tcatgattac acctgtaatg gcg                          43

SEQ ID NO: 99             moltype = DNA   length = 42
FEATURE                   Location/Qualifiers
source                    1..42
                          mol_type = other DNA
                          organism = synthetic construct
SEQUENCE: 99
gaaacacaag gtgaatttgt tccccaccat gataccccca tg                           42

SEQ ID NO: 100            moltype = DNA   length = 20
```

-continued

```
FEATURE           Location/Qualifiers
source            1..20
                  mol_type = other DNA
                  organism = synthetic construct
SEQUENCE: 100
tgcttttggc ggtgcattag                                        20

SEQ ID NO: 101    moltype = DNA   length = 19
FEATURE           Location/Qualifiers
source            1..19
                  mol_type = other DNA
                  organism = synthetic construct
SEQUENCE: 101
tccgtaggtg aacctgcgg                                         19

SEQ ID NO: 102    moltype = DNA   length = 20
FEATURE           Location/Qualifiers
source            1..20
                  mol_type = other DNA
                  organism = synthetic construct
SEQUENCE: 102
tcctccgctt attgatatgc                                        20

SEQ ID NO: 103    moltype = DNA   length = 19
FEATURE           Location/Qualifiers
source            1..19
                  mol_type = other DNA
                  organism = synthetic construct
SEQUENCE: 103
gtagtcatat gcttgtctc                                         19

SEQ ID NO: 104    moltype = DNA   length = 20
FEATURE           Location/Qualifiers
source            1..20
                  mol_type = other DNA
                  organism = synthetic construct
SEQUENCE: 104
cttccgtcaa ttcctttaag                                        20

SEQ ID NO: 105    moltype = DNA   length = 19
FEATURE           Location/Qualifiers
source            1..19
                  mol_type = other DNA
                  organism = synthetic construct
SEQUENCE: 105
gtacccgctg aacttaagc                                         19

SEQ ID NO: 106    moltype = DNA   length = 17
FEATURE           Location/Qualifiers
source            1..17
                  mol_type = other DNA
                  organism = synthetic construct
SEQUENCE: 106
atcctgaggg aaacttc                                           17

SEQ ID NO: 107    moltype = DNA   length = 25
FEATURE           Location/Qualifiers
source            1..25
                  mol_type = other DNA
                  organism = synthetic construct
SEQUENCE: 107
taacaactgc tgggccaagg gtcac                                  25

SEQ ID NO: 108    moltype = DNA   length = 21
FEATURE           Location/Qualifiers
source            1..21
                  mol_type = other DNA
                  organism = synthetic construct
SEQUENCE: 108
tctggatgtt gttgggaatc c                                      21

SEQ ID NO: 109    moltype = DNA   length = 23
FEATURE           Location/Qualifiers
source            1..23
                  mol_type = other DNA
                  organism = synthetic construct
SEQUENCE: 109
atcatgtttg agaccttcaa cac                                    23
```

-continued

```
SEQ ID NO: 110          moltype = DNA   length = 21
FEATURE                 Location/Qualifiers
source                  1..21
                        mol_type = other DNA
                        organism = synthetic construct
SEQUENCE: 110
catctcttgc tcgaagtcca g                                              21

SEQ ID NO: 111          moltype = DNA   length = 20
FEATURE                 Location/Qualifiers
source                  1..20
                        mol_type = other DNA
                        organism = synthetic construct
SEQUENCE: 111
ggttcaagtc cctctatccc                                                20

SEQ ID NO: 112          moltype = DNA   length = 20
FEATURE                 Location/Qualifiers
source                  1..20
                        mol_type = other DNA
                        organism = synthetic construct
SEQUENCE: 112
atttgaactg gtgacacgag                                                20

SEQ ID NO: 113          moltype = DNA   length = 19
FEATURE                 Location/Qualifiers
source                  1..19
                        mol_type = other DNA
                        organism = synthetic construct
SEQUENCE: 113
ctcggtgttg atgaggatt                                                 19

SEQ ID NO: 114          moltype = DNA   length = 19
FEATURE                 Location/Qualifiers
source                  1..19
                        mol_type = other DNA
                        organism = synthetic construct
SEQUENCE: 114
cccctgaaat acacaacct                                                 19

SEQ ID NO: 115          moltype = DNA   length = 44
FEATURE                 Location/Qualifiers
source                  1..44
                        mol_type = other DNA
                        organism = synthetic construct
SEQUENCE: 115
tgctcttaaa tggcccattg aatattgatc ggagatgttc cagg                     44

SEQ ID NO: 116          moltype = DNA   length = 41
FEATURE                 Location/Qualifiers
source                  1..41
                        mol_type = other DNA
                        organism = synthetic construct
SEQUENCE: 116
tcatcgtggt ggttattgtt ggttttgtaa aacgcgttcg c                        41

SEQ ID NO: 117          moltype = DNA   length = 20
FEATURE                 Location/Qualifiers
source                  1..20
                        mol_type = other DNA
                        organism = synthetic construct
SEQUENCE: 117
tgtttatagg attaaaacct                                                20

SEQ ID NO: 118          moltype = DNA   length = 23
FEATURE                 Location/Qualifiers
source                  1..23
                        mol_type = other DNA
                        organism = synthetic construct
SEQUENCE: 118
gtcacctgcg ttttatggac acg                                            23
```

1

METHOD FOR DETECTING A TARGETED NUCLEIC ACID FROM A DEOXYRIBONUCLEIC ACID (DNA) SAMPLE EXTRACTED USING A DNA EXTRACTION KIT THROUGH DNA AMPLIFICATION TESTING

INCORPORATION BY REFERENCE OF MATERIAL SUBMITTED ELECTRONICALLY

The Sequence Listing, which is a part of the present disclosure, is submitted concurrently with the specification as an XML file in compliance with 37 CFR 1.831-1.835. The contents of the electronic sequence listing (APC_001_Seqlisting.xml; size: 105,811 bytes; and date of creation: Jul. 22, 2025) is herein incorporated by reference in its entirety.

FIELD OF THE INVENTION

The present invention relates to a method and kit for detecting a targeted nucleic acid from DNA samples extracted using a DNA extraction kit via DNA amplification techniques. More specifically, the invention provides a dipstick-based DNA extraction method and its use with various amplification methods including PCR, real-time PCR, colorimetric LAMP, and real-time LAMP to detect the targeted nucleic acid in diverse biological samples such as blood, tissue, bacterial, fungal, plant, and swab samples. The invention further encompasses optimized reagent formulations and primer sets for the rapid, sensitive, and specific detection of pathogens such as African swine fever virus (ASFV), *Neisseria meningitidis*, as well as host genes such as beta actin or fungal rDNA regions (SSU, LSU, ITS) and tubulin, depending on the application.

BACKGROUND ART

Traditional methods for nucleic acid extraction, such as phenol-chloroform extraction and silica column-based techniques, typically involve labor-intensive, multi-step protocols that require specialized equipment and trained personnel. These conventional methods not only prolong the time needed to obtain purified DNA but, in some cases, the quality of nucleic acid obtained from these techniques is not suitable for subsequent nucleic acid amplification reactions. Moreover, for certain specialized amplification techniques, the quality of DNA produced by these methods may be inadequate.

In recent years, dipstick-based extraction methods have been developed as simpler and more rapid alternatives for extracting nucleic acids from complex biological samples. Specifically, this method provides a solution for nucleic acid collection at the point of care. However, existing dipstick methods often fail to deliver DNA of sufficient purity and yield for demanding applications, such as colorimetric LAMP with phenol red, particularly when processing diverse sample types including blood, animal tissue, plant tissue, fungal tissue, bacterial cultures, or swab samples. A major challenge remains in developing an extraction method that consistently produces high-quality DNA free of inhibitory contaminants while maintaining a streamlined workflow.

Rapid diagnosis of pathogens (e.g., African Swine Fever Virus (ASFV), *Neisseria meningitidis* bacteria), as well as molecular identification, qualitative, and quantitative analysis of genes such as beta-actin, SSU, LSU, ITS, tubulin, at the point of care or in fully equipped laboratories, requires a robust, sensitive, and specific amplification platform. The performance of these amplification reactions is heavily dependent on the integrity and purity of the extracted nucleic acid. Inadequate extraction may lead to false-negative results, reduced assay sensitivity, weakened disease surveillance and outbreak control capabilities, or inaccurate molecular identification, qualitative, and quantitative results.

Therefore, there is a need for a dipstick-based DNA extraction method designed to yield high-quality DNA suitable for various amplification techniques, including PCR, real-time PCR, colorimetric LAMP, and real-time LAMP, across a wide range of biological sample types.

Furthermore, it is necessary to provide a dipstick-based DNA extraction and detection workflow that overcomes the multi-step complexity of traditional phenol-chloroform and column-based methods, while remaining simple enough for point-of-care.

Accordingly, the present invention provides a method for detecting a targeted nucleic acid from a deoxyribonucleic acid (DNA) sample extracted using a DNA extraction kit through DNA amplification testing comprising: (i) preparing a DNA extraction kit and a test sample; (ii) adding the test sample to the tube containing the lysis buffer, shaking and incubating to obtain a sample-containing tube; (iii) shaking the sample-containing tube, then immersing the dipstick into the sample-containing tube to obtain a sample-loaded dipstick; (iv) transferring the sample-loaded dipstick into the tube containing the wash buffer, removing excess wash buffer from the dipstick to obtain a dipstick containing the DNA from the test sample; and (v) amplifying the DNA from the dipstick containing the DNA of the test sample using a DNA amplification technique and reading the result to detect the targeted nucleic acid.

Finally, this method not only streamlines nucleic acid extraction but also delivers rapid, reliable diagnostics essential for timely disease surveillance and outbreak management in both laboratory and field settings. In addition, this method provides a solution for molecular diagnosis, qualitative and quantitative analysis of genes, effectively applicable in both laboratory and field settings.

This invention provides solutions to achieve the above goals.

SUMMARY OF THE INVENTION

Accordingly, an objective of the present invention is to provide a method for detecting a targeted nucleic acid from a deoxyribonucleic acid (DNA) sample extracted using a DNA extraction kit through DNA amplification testing comprising steps performed in the following specific order:

(i) preparing a DNA extraction kit and a test sample, wherein:

(A1) the DNA extraction kit comprising: a 1.5 mL tube containing from 230 to 250 μL of a lysis buffer, a 1.5 mL tube containing 200 μL of a wash buffer, and a dipstick;

wherein the lysis buffer has a pH of 8 and contains 1 mM Tris-HCl, 25 mM NaCl, 2.5 mM EDTA, and 0.05% SDS;

wherein the wash buffer has a pH of 8 and contains 0.75 mM Tris-HCl;

wherein the dipstick is prepared by performing steps from (a1) to (d1):

(a1) cutting a sheet of qualitative filter paper having an 11 μm pore size into paper strips each 56 mm long, 2 mm wide, and 0.18 mm thick;

(b1) applying an adhesive decal to one end of each paper strip of step (a1) to obtain a decal-treated strip comprising:

a first region 50 mm long, 2 mm wide, and 0.3 mm thick bearing the decal on both faces; and a second region 6 mm long, 2 mm wide, and 0.18 mm thick left undecorated;

(c1) immersing each decal-treated strip in molten paraffin wax for 10 seconds, then drying at 28° C. to 32° C. to obtain a paraffin-treated strip comprising three adjacent portions:
   a handle portion corresponding to the decal-treated first region, 50 mm long, 2 mm wide, and 0.4-0.5 mm thick;
   a fluid-barrier portion 3 mm long, 2 mm wide, and 0.2-0.3 mm thick; and
   a nucleic acid-capture portion corresponding to the undecorated second region, 3 mm long, 2 mm wide, and 0.18 mm thick;
(d1) irradiating both faces of each paraffin-treated strip of step (c1) with ultraviolet light for 15 minutes per side to obtain the dipstick;
(B1) the test sample is selected from the group comprising: a blood sample, a clinical specimen, a swab sample, an animal tissue sample, a plant tissue sample, a fungal tissue sample, a soil sample, and a water sample;
   wherein the swab sample is prepared by:
      inserting an end of a swab into a site on the subject's body containing biological fluid;
      rotating the swab at the collection site for 10-20 seconds under light pressure so as to maximize adhesion of the sample onto the swab tip; and
      withdrawing the swab and air-drying it at 28° C. to 32° C. for 30 minutes to obtain the swab sample;
   wherein the animal tissue sample is prepared by grinding 0.5 g of animal tissue for 10 minutes, adding 500 μL of the lysis buffer, and continuing to grind until a homogeneous mixture is formed;
   wherein the plant tissue sample is prepared by grinding 0.5 g of plant tissue for 20 minutes, adding 500 μL of the lysis buffer, and continuing to grind until a homogeneous mixture is formed;
   wherein the fungal tissue sample is prepared by grinding 0.5 g of fungal tissue for 10 minutes, adding 500 μL of the lysis buffer, and continuing to grind until a homogeneous mixture is formed;
(ii) adding an amount of the test sample to the 1.5 mL tube containing from 230 to 250 μL of the lysis buffer, shaking for 30 seconds, and incubating at 28° C. to 37° C. for 5 minutes to obtain a sample-containing tube;
   wherein the blood sample is added in an amount of 20 μL;
   wherein each of the clinical specimen, the animal tissue sample, the plant tissue sample, and the fungal tissue sample is added in an amount of 20 mg the homogeneous mixture;
   wherein the swab sample is immersed into the lysis buffer;
(iii) shaking the sample-containing tube for 30 seconds, then immersing the dipstick into the sample-containing tube and holding it in place for 10-15 seconds to obtain a sample-loaded dipstick;
(iv) transferring the sample-loaded dipstick into the 1.5 mL tube containing 200 μL of the wash buffer, holding the dipstick in the wash buffer for 5 seconds, and then removing excess wash buffer from the dipstick by wiping the dipstick against the inner wall of the tube to obtain a dipstick containing the DNA of the test sample; and
(v) amplifying the DNA from the dipstick containing the DNA of the test sample using a DNA amplification technique and reading the result to detect the targeted nucleic acid;
   wherein the amplification technique is selected from the group consisting of: a polymerase chain reaction (PCR), a real-time PCR, a colorimetric loop-mediated isothermal amplification (LAMP), and a real-time LAMP.

Moreover, the invention provides methods for detecting the targeted nucleic acid from DNA samples extracted from a wide range of sample types including pig blood, pig tissue, clinical specimens, fungal tissue, swab samples, and plant tissue. The DNA samples are amplified using PCR, real-time PCR, colorimetric LAMP, and real-time LAMP.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Figure 1:
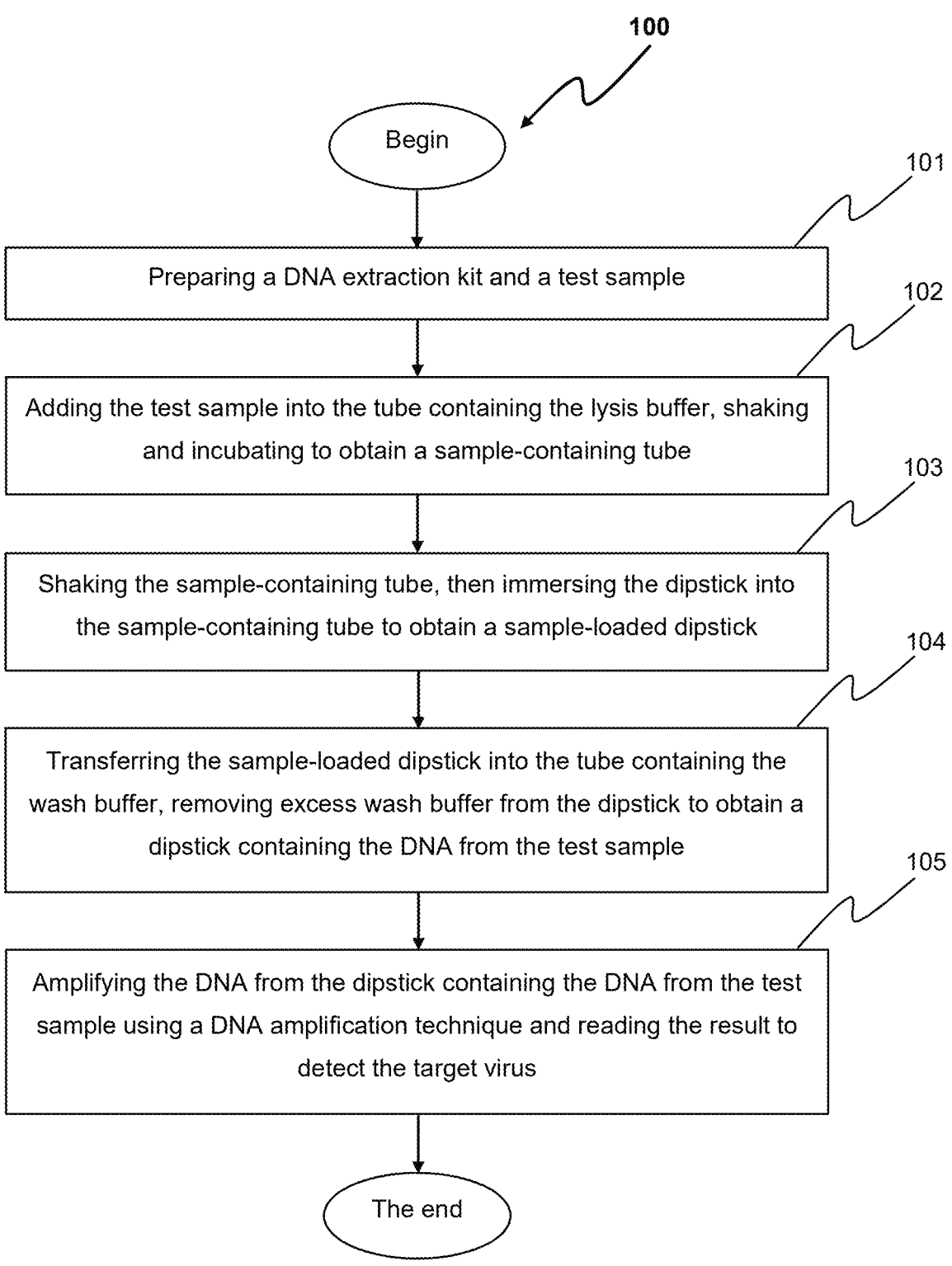
FIG. 1 is a flowchart illustrating a method for detecting a targeted nucleic acid from a deoxyribonucleic acid (DNA) sample extracted using a DNA extraction kit through DNA amplification testing 100 according to the embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Within the scope of this invention, the term "qualitative filter paper" refers to a porous material made from cellulose fibers or biopolymer compounds with absorbent properties. It is designed to retain insoluble solid particles in a solution while allowing liquid to pass through via capillary action. Qualitative filter paper is chemically inert, meaning it does not react with biological components in the test sample, ensuring the stability of the nucleic acid extraction process. Additionally, it possesses sufficient mechanical strength to maintain its shape during handling and has the ability to retain and release nucleic acids when exposed to a wash solution, ensuring efficient DNA/RNA recovery for subsequent amplification and analysis procedures.

Within the scope of this invention, the term "decal" refers to a thin, flexible polymer film laminated with a pressure-sensitive adhesive on both faces, which when applied to filter-paper strips increases handle stiffness.

Within the scope of this invention, the term "blood sample" refers to whole blood or blood components obtained from an animal subject using standard blood collection techniques.

Within the scope of this invention, the term "clinical specimen" refers to any biological fluid other than blood collected from a human or animal body, including but not limited to pharyngeal fluid, urine, cerebrospinal fluid, pleural fluid, synovial fluid, sputum, or wound exudate.

Within the scope of this invention, the term "swab sample" refers to a biological specimen collected using a sterile swab to absorb fluid from a site on the body of a human or animal containing biological secretions.

Within the scope of this invention, the term "animal tissue sample" refers to a solid tissue obtained from an animal body, including but not limited to muscle tissue, liver tissue, skin tissue, or internal organ tissue.

Within the scope of this invention, the term "plant tissue sample" refers to a solid tissue derived from a plant, including but not limited to leaf, stem, root, or fruit tissue.

Within the scope of this invention, the term "fungal tissue sample" refers to a tissue obtained from a fungus, including but not limited to the fruiting body or the mycelial network.

Referring to FIG. 1 is a flowchart illustrating a method for detecting a targeted nucleic acid from a deoxyribonucleic acid (DNA) sample extracted using a DNA extraction kit through DNA amplification testing 100 ("method 100"). Method 100 begins with step 101 preparing a DNA extraction kit and a test sample.

In the present invention, the DNA extraction kit comprising: a 1.5 mL tube containing from 230 to 250 μL of a lysis buffer, a 1.5 mL tube containing 200 μL of a wash buffer, and a dipstick;

wherein the lysis buffer has a pH of 8 and contains 1 mM Tris-HCl, 25 mM NaCl, 2.5 mM EDTA, and 0.05% SDS;

wherein the wash buffer has a pH of 8 and contains 0.75 mM Tris-HCl;

wherein the dipstick is prepared by performing steps from (a1) to (d1):

(a1) cutting a sheet of qualitative filter paper having an 11 μm pore size into paper strips each 56 mm long, 2 mm wide, and 0.18 mm thick;

(b1) applying an adhesive decal to one end of each paper strip of step (a1) to obtain a decal-treated strip comprising:

a first region 50 mm long, 2 mm wide, and 0.3 mm thick bearing the decal on both faces; and a second region 6 mm long, 2 mm wide, and 0.18 mm thick left undecorated;

(c1) immersing each decal-treated strip in molten paraffin wax for 10 seconds, then drying at 28° C. to 32° C. to obtain a paraffin-treated strip comprising three adjacent portions:

a handle portion corresponding to the decal-treated first region, 50 mm long, 2 mm wide, and 0.4-0.5 mm thick;

a fluid-barrier portion 3 mm long, 2 mm wide, and 0.2-0.3 mm thick; and a nucleic acid-capture portion corresponding to the undecorated second region, 3 mm long, 2 mm wide, and 0.18 mm thick;

(d1) irradiating both faces of each paraffin-treated strip of step (c1) with ultraviolet light for 15 minutes per side to obtain the dipstick.

Figure 2:
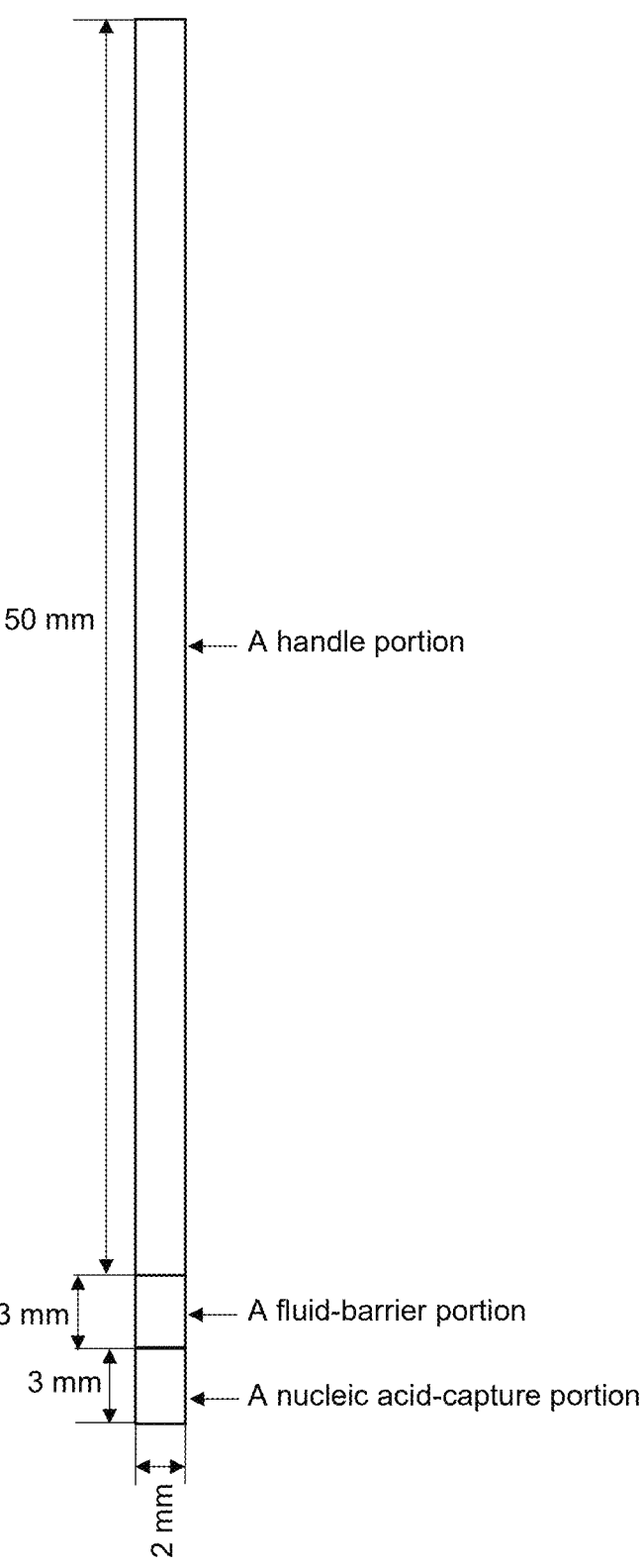
FIG. 2 is a schematic Illustration of the dipstick.

Referring to FIG. 2, there is shown a two-dimensional schematic illustration of the dipstick.

In the present invention, the test sample is selected from the group comprising: a blood sample, a clinical specimen, a swab sample, an animal tissue sample, a plant tissue sample, a fungal tissue sample, a soil sample, and a water sample;

wherein the swab sample is prepared by:

inserting an end of a swab into a site on the subject's body containing biological fluid;

rotating the swab at the collection site for 10-20 seconds under light pressure so as to maximize adhesion of the sample onto the swab tip; and withdrawing the swab and air-drying it at 28° C. to 32° C. for 30 minutes to obtain the swab sample;

wherein the animal tissue sample is prepared by grinding 0.5 g of animal tissue for 10 minutes, adding 500 μL of the lysis buffer, and continuing to grind until a homogeneous mixture is formed;

wherein the plant tissue sample is prepared by grinding 0.5 g of plant tissue for 20 minutes, adding 500 μL of the lysis buffer, and continuing to grind until a homogeneous mixture is formed;

wherein the fungal tissue sample is prepared by grinding 0.5 g of fungal tissue for 10 minutes, adding 500 μL of the lysis buffer, and continuing to grind until a homogeneous mixture is formed;

At step 102, adding an amount of the test sample into the 1.5 mL tube containing from 230 to 250 μL of the lysis buffer, shaking the tube for 30 seconds, and incubating at a temperature of 28° C.-37° C. for 5 minutes to obtain a sample-containing tube;

wherein the blood sample is added in an amount of 20 μL;

wherein each of the clinical specimen, the animal tissue sample, the plant tissue sample, and the fungal tissue sample is added in an amount of 20 mg;

wherein the swab sample is immersed into the lysis buffer.

At step 103, shaking the sample-containing tube for 30 seconds, then immersing the dipstick into the sample-containing tube and holding it in place for 10-15 seconds to obtain a sample-loaded dipstick.

At step 104, transferring the sample-loaded dipstick into the 1.5 mL tube containing 200 μL of the wash buffer, holding the dipstick in the wash buffer for 5 seconds, and then removing excess wash buffer from the dipstick by wiping the dipstick against the inner wall of the tube to obtain a dipstick containing the DNA of the test sample.

Finally, at step 105, amplifying the DNA from the dipstick containing the DNA of the test sample using a DNA amplification technique and reading the result to detect the targeted nucleic acid; wherein the amplification technique is selected from the group consisting of: a polymerase chain reaction (PCR), a real-time PCR, a colorimetric loop-mediated isothermal amplification (LAMP), and a real-time LAMP.

The concentration of Tris-HCl in the lysis buffer and wash buffer plays a crucial role in nucleic acid extraction from biological samples and ensures the efficiency of the colorimetric LAMP. The Tris-HCl concentration was selected based on experimental results evaluating the impact of different Tris-HCl concentrations on the effectiveness of the colorimetric LAMP.

Reference Table 1, which presents the results of ASFV (African swine fever virus) detection in pigs using the colorimetric LAMP. The experiment utilized eight types of lysis buffers and two types of wash buffers to extract DNA from pig blood samples.

TABLE 1

| Colorimetric LAMP results for ASFV detection using different lysis and wash buffers | | | | | | | | |
|---|---|---|---|---|---|---|---|---|
| | Lysis Buffer | | | | | | | |
| Wash Buffer | LB 1 | LB 2 | LB 3 | LB 4 | LB 5 | LB 6 | LB 7 | LB 8 |
| WB 1 | — | — | — | — | — | — | — | — |
| WB 2 | — | — | — | — | — | — | — | — | in which: (—) indicates no reaction occurred;
LB 1 contains 0.1M Tris-HCl, 0.2 M NaCl, 5 mM EDTA, and 1% (v/v) SDS;
LB 2 contains 0.5M NaCl and 1% (v/v) SDS;
LB 3 contains 20 mM Tris-HCl, 25 mM NaCl, 2.5 mM EDTA, and 0.05% (v/v) SDS;
LB 4 contains 0.4M Tris-HCl, 0.15 M NaCl, 5 mM EDTA, and 0.1% (v/v) SDS;
LB 5 contains 50 mM Tris-HCl, 800 mM GuHCl, 0.5% (v/v) Triton X-100, and 1% (v/v) Tween 20;
LB 6 contains 50 mM Tris-HCl, 100 mM NaCl, 5 mM EDTA, 1.5 M GuHCl, and 1% (v/v) Tween 20;
LB 7 contains 10 mM Tris-HCl, 1 mM EDTA, and 2 mg/mL proteinase K;
LB 8 contains 1 mM Tris-HCl, 25 mM NaCl, 2.5 mM EDTA, and 0.05% SDS.
WB 1 contains 10 mM Tris-HCl and 0.1% (v/v) Tween 20;
WB 2 contains 10 mM Tris-HCl.

Based on the results in Table 1, it can be observed that the use of different lysis buffers with varying Tris-HCl concentrations (ranging from 1 mM to 0.1 M), in combination with two types of wash buffers containing 10 mM Tris-HCl (one containing Tween 20 and one without), did not result in a successful colorimetric LAMP (indicated by "–"). This suggests that high concentrations of Tris-HCl in the solutions may create a suboptimal reaction environment.

Reference Table 2, which presents the results of ASFV (African swine fever virus) detection in pigs using the colorimetric LAMP. The experiment was conducted with a lysis buffer containing a low Tris-HCl concentration (1 mM) and tested with 10 different wash buffers.

TABLE 2

| Colorimetric LAMP results using a low Tris-HCl concentration lysis buffer combined with different wash buffers | | | | | | | | | | |
|---|---|---|---|---|---|---|---|---|---|---|
| Experimental condition | WB 1 | WB 2 | WB 3 | WB 4 | WB 5 | WB 6 | WB 7 | WB 8 | WB 9 | WB 10 | C_ |
| LB 8 | + | + | + | + | + | + | + | + | + | + | – |
| Color change time (minutes) | 25 | 25 | 25 | 25 | 25 | 15 | 20 | 25 | 25 | 25 | | in which:
(+) indicates the reaction occurred;
WB 1 contains Tris-HCl 0.25 mM (pH 8.0), Tween 20 0.1%;
WB 2 contains Tris-HCl 0.25 mM (pH 8.0);
WB 3 contains Tris-HCl 0.5 mM (pH 8.0), Tween 20 0.1%;
WB 4 contains Tris-HCl 0.5 mM (pH 8.0);
WB 5 contains Tris-HCl 0.75 mM (pH 8.0), Tween 20 0.1%;
WB 6 contains Tris-HCl 0.75 mM (pH 8.0);
WB 7 contains Tris-HCl 1 mM (pH 8.0), Tween 20 0.1%;
WB 8 contains Tris-HCl 1 mM (pH 8.0);
WB 9 contains Tween 20 0.1%;
WB 10 contains water;
LB 8 contains Tris-HCl 1 mM, NaCl 25 mM, EDTA 2.5 mM, SDS 0.05%;
C_ is the negative control.

The results in Table 2 show that when using Lysis Buffer 8 (LB8) in combination with 10 different Wash Buffers (WB1 to WB10), all conditions resulted in a successful colorimetric LAMP (indicated by the "+" symbol, meaning color change occurred), with color change times ranging from 15 to 25 minutes. Notably, the condition using Wash Buffer 6 (WB6) achieved the fastest color change, in just 15 minutes, suggesting that the components of WB6 interact well with LB8, effectively removing impurities or inhibitors while maintaining optimal conditions for enzyme activity in the colorimetric LAMP. In Lysis Buffer 8 (Tris-HCl 1 mM, NaCl 25 mM, EDTA 2.5 mM, SDS 0.05%), the Tris-HCl concentration is maintained at 1 mM, ensuring pH stability without affecting the subsequent detection of the amplified products in the colorimetric LAMP reaction. The SDS concentration (0.05%) is sufficient to lyse cell membranes and release DNA, yet low enough to minimize the risk of residual SDS interfering with the LAMP. EDTA (2.5 mM) functions to inactivate DNases by chelating $Mg^{2+}$ ions, but does not excessively deplete $Mg^{2+}$ required for polymerase activity. Additionally, NaCl (25 mM) helps stabilize DNA and disrupt protein-nucleic acid interactions. Meanwhile, Wash Buffer 6 (Tris-HCl 0.75 mM, pH 8.0) maintains a moderate Tris concentration, ensuring stable pH without affecting the subsequent detection of the amplified products in the colorimetric LAMP reaction while omitting Tween 20, which could potentially reduce the amplification efficiency of colorimetric LAMP. This combination facilitates efficient DNA extraction and colorimetric LAMP, preserving enzyme activity and enhancing the reliability of the results.

According to the preferred embodiment of the present invention, the DNA amplification technique is the colorimetric LAMP using phenol red as an indicator to monitor the reaction. Wherein the colorimetric LAMP is performed according to the following steps:

(A2) preparing a DNA amplification solution by mixing a reaction solution with a primer solution at a ratio of 9:1 (v/v), wherein the reaction solution comprises a colorimetric LAMP master mix (WarmStart® colorimetric LAMP 2× master mix) at a 1× concentration, trehalose at a concentration of 0.45 M, and guanidine hydrochloride (GuHCl) at a concentration of 0.04 M; and (B2) amplifying the test sample and reading the result by performing the following steps from (a2) to (d2):

(a2) pipetting 5 µL of the DNA amplification solution into the bottom of a tube, then sealing the tube to obtain a tube containing the DNA amplification solution;

(b2) immersing the test sample by dipping the dipstick containing DNA of the test sample into the tube of step (a2) for 5 seconds, removing excess solution by touching the tube wall, then sealing the tube to obtain a sample-loaded tube; wherein the sample-loaded tube appears red-pink;

(c2) incubating the sample-loaded tube in a heating device under the following thermal conditions: 25° C. for 2 minutes, followed by 65° C. for 40-50 minutes, to obtain a processed tube; and (d2) reading the result to detect the targeted nucleic acid, wherein:

a positive result is indicated when the processed tube changes to yellow; and a negative result is indicated when the processed tube remains red-pink.

According to the preferred embodiment of the present invention, wherein the DNA amplification technique is the real-time LAMP is performed according to the following steps:

(A3) preparing a tube containing a real-time LAMP solution by mixing 1 µL of a isothermal amplification buffer at a 10× concentration, 0.6 µL of $MgSO_4$, 1 µL of a LAMP primer set solution at a 10× concentration, 0.4 µL of a DNA polymerase solution at a 8 U/µL concentration, 0.6 µL of a guanidine hydrochloride solution at a 0.5 M concentration, 1.4 µL of dNTPs at a 40 mM concentration, and 0.5 µL of a fluorescent dye at a 20× concentration;

(B3) amplifying the test sample and reading the result by performing the following steps from (a3) to (c3):

(a3) immersing the test sample by dipping the dipstick containing DNA of the test sample into the tube of step (A3) for 5 seconds, removing excess solution by touching the tube wall, then sealing the tube to obtain a sample-loaded reaction tube;

(b3) placing the sample-loaded reaction tube in a real-time LAMP instrument and running the following thermal program:

step 1: 66° C. for 10 minutes; and step 2: 66° C. for 1 minute for 80 cycles; and (c3) reading the result on the real-time LAMP instrument, wherein a positive result is indicated by the appearance of an amplification curve and a characteristic melting-curve peak; and a negative result is indicated by the absence of an amplification curve or a characteristic melting-curve peak.

According to the preferred embodiment of the present invention, test sample is a pig blood sample (*Sus scrofa domesticus* Brisson) extracted to detect an African swine fever virus (ASFV) by the colorimetric LAMP using phenol red as an indicator to monitor the reaction, comprising the steps of:

(A4) preparing a DNA amplification solution by mixing a reaction solution with a LAMP-1 primer set solution at a ratio of 9:1 (v/v); wherein the reaction solution comprises a colorimetric LAMP 2× master mix (WarmStart® colorimetric LAMP 2× master mix) at a 1× concentration, trehalose at a 0.45 M concentration, and guanidine hydrochloride (GuHCl) at a 0.04 M concentration;

the LAMP-1 primer set solution comprises a LAMP-1-F3 primer solution at a 0.2 µM concentration, a LAMP-1-B3 primer solution at a 0.2 µM concentration, a LAMP-1-FIP primer solution at a 1.6 µM concentration, a LAMP-1-BIP primer solution at a 1.6 µM concentration, a LAMP-1-LF primer solution at a 0.4 µM concentration, and a LAMP-1-LB primer solution at a 0.4 µM concentration; wherein the LAMP-1-F3 primer has the sequence set forth in SEQ ID NO. 1;

the LAMP-1-B3 primer is selected from the sequences set forth in SEQ ID NOs. 2 to 5;

the LAMP-1-FIP primer is selected from the sequences set forth in SEQ ID NOs. 6 to 21;

the LAMP-1-BIP primer is selected from the sequences set forth in SEQ ID NOs. 22 to 53;

the LAMP-1-LF primer is selected from the sequences set forth in SEQ ID NOs. 54 to 69; and the LAMP-1-LB primer is selected from the sequences set forth in SEQ ID NOs. 70 to 77;

(B4) amplifying the test sample and reading the result by performing the following steps from (a4) to (d4):

(a4) pipetting 5 μL of the DNA amplification solution into the bottom of a tube, then sealing the tube to obtain a tube containing the DNA amplification solution;

(b4) immersing the test sample by dipping the dipstick containing the DNA of the pig blood sample into the tube from step (a4) for 5 seconds, removing excess solution by touching the tube wall, then sealing the tube to obtain a sample-loaded tube; wherein the sample-loaded tube appears red-pink;

(c4) incubating the sample-loaded tube in a heating device under the following thermal conditions: 25° C. for 2 minutes, followed by 65° C. for 40-50 minutes, to obtain a processed tube; and (d4) reading the result to detect the target virus, wherein:

a positive result is indicated when the processed tube changes to yellow; and a negative result is indicated when the processed tube remains red-pink.

Method 100 is applied to detect the B646L gene of African swine fever virus (ASFV) from DNA extracted from the pig blood sample (*Sus scrofa domesticus* Brisson) using the colorimetric LAMP with phenol red as an indicator to monitor the reaction process, comparing the efficiency of three primer sets: LAMP-1 (this primer set was custom-designed), LAMP-3 (primer sequences referenced from Tao et al., 2020[11]), and LAMP-5 (primer sequences referenced from Bo et al., 2021[21]). Specifically, the LAMP-1 primer set includes LAMP-1-F3 with the sequence set forth in SEQ ID NO. 1, LAMP-1-B3 with the sequence set forth in SEQ ID NO. 2, LAMP-1-FIP with the sequence set forth in SEQ ID NO. 6, LAMP-1-BIP with the sequence set forth in SEQ ID NO. 22, LAMP-1-LF with the sequence set forth in SEQ ID NO. 54, and LAMP-1-LB with the sequence set forth in SEQ ID NO. 70. The LAMP-3 primer set includes LAMP-3-F3 with the sequence set forth in SEQ ID NO. 82, LAMP-3-B3 with the sequence set forth in SEQ ID NO. 83, LAMP-3-FIP with the sequence set forth in SEQ ID NO. 84, LAMP-3-BIP with the sequence set forth in SEQ ID NO. 85, LAMP-3-LF with the sequence set forth in SEQ ID NO. 86, and LAMP-3-LB with the sequence set forth in SEQ ID NO. 87. The LAMP-5 primer set includes LAMP-5-F3 with the sequence set forth in SEQ ID NO. 113, LAMP-5-B3 with the sequence set forth in SEQ ID NO. 114, LAMP-5-FIP with the sequence set forth in SEQ ID NO. 115, LAMP-5-BIP with the sequence set forth in SEQ ID NO. 116, LAMP-5-LF with the sequence set forth in SEQ ID NO. 117, and LAMP-5-LB with the sequence set forth in SEQ ID NO. 118.

Reference to Table 3 presents the results of method 100, which extracts DNA from a pig blood sample (*Sus scrofa domesticus* Brisson) to detect African swine fever virus (ASFV) using the colorimetric LAMP with phenol red as an indicator to monitor the reaction process, comparing the efficiency of three primer sets: LAMP-1, LAMP-3, and LAMP-5.

TABLE 3

| The results of ASFV detection using the colorimetric LAMP method with primer sets LAMP-1, LAMP-3, and LAMP-5 | | | | | | | | | |
|---|---|---|---|---|---|---|---|---|---|
| Experimental | LAMP-1 | | | LAMP-3 | | | LAMP-5 | | |
| condition | M1 | M2 | C1 | M1' | M2' | C2 | M1" | M2" | C3 |
| After 30 minutes | + | + | − | + | + | − | + | + | − | in which: M1, M1', M1" are test samples containing $10^4$ copies of the ASFV B646L gene;
M2, M2', M2" are test samples containing $10^5$ copies of the ASFV B646L gene;
C1, C2, C3 are negative control samples;
(−) no reaction occurred;
(+) reaction occurred.

Based on Table 3, all three primer sets LAMP-1, LAMP-3, and LAMP-5 produced positive colorimetric LAMPs for both $10^4$ and $10^1$ copy ASFV B646L templates within 30 minutes, while all negative controls (C1, C2, C3) remained unchanged throughout the assay.

According to the preferred embodiment of the present invention, the test sample is a pig blood sample (*Sus scrofa domesticus* Brisson) extracted to detect an African swine fever virus (ASFV) by the PCR, comprising the steps of:

(A5) preparing a tube containing a PCR solution by mixing 2 μL of a qPCR mix solution (5× HOT FIRE-PoI® SolisGreen® qPCR mix) at a 5× concentration, 0.4 μL of a P1 primer solution at a 10 μM concentration, 0.4 μL of a P2 primer solution at a 10 μM concentration, 0.6 μL of a betaine solution at a 5 M concentration, 0.15 μL of dimethyl sulfoxide (DMSO), and 6.45 μL of ultrapure water; wherein the P1 primer has the sequence set forth in SEQ ID NO. 78; and the P2 primer has the sequence set forth in SEQ ID NO. 79;

(B5) amplifying the test sample and reading the result by performing the following steps from (a5) to (c5):

(a5) immersing the test sample by dipping the dipstick containing DNA of the pig blood sample into the tube of step (A5) for 5 seconds, removing excess solution by touching the tube wall, then sealing the tube to obtain a sample-loaded reaction tube;

(b5) placing the sample-loaded reaction tube in a thermocycler and running the following program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes; and (c5) analyzing the amplification products by agarose gel electrophoresis using a 1.5% agarose gel in 1×TAE buffer at 100 V for 45 minutes, staining with a nucleic acid gel stain solution (GelRed® nucleic acid gel stain), and visualizing under UV illumination; wherein a positive result is indicated by the presence of a DNA band at approximately 257 base pairs, and a negative result is indicated by the absence of a DNA band at approximately 257 base pairs.

Figure 3:
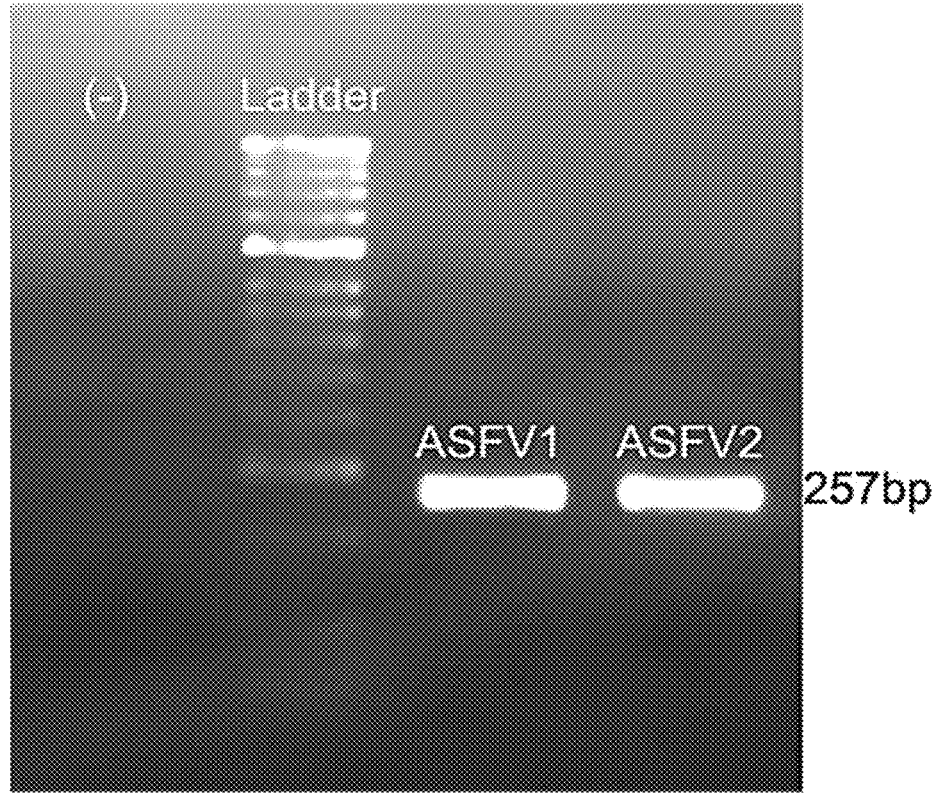
FIG. 3 shows the PCR result for detecting the B646L gene of ASFV in the pig blood samples.

Method 100 is applied to detect the B646L gene of African swine fever virus (ASFV) from DNA extracted from the pig blood sample (*Sus scrofa domesticus* Brisson) by the PCR. The primer set used for the PCR comprises the P1 primer and the P2 primer, the sequences of which are referenced from Aguero et al., 2003[3]. FIG. 3 presents an image of the PCR results for detecting the B646L gene of ASFV in the pig blood sample. The results indicate that the two samples, ASFV1 and ASFV2, exhibit clear amplification bands, demonstrating that method 100 successfully yields a sufficient amount of target DNA for detecting the B646L gene of ASFV. This confirms the efficiency of the extraction process and the specificity of the PCR in detecting ASFV from pig blood samples.

According to the preferred embodiment of the present invention, the test sample is a pig blood sample (*Sus scrofa domesticus* Brisson) extracted to detect an African swine fever virus (ASFV) by the real-time PCR, comprising the steps of:

(A6) preparing a tube containing a real-time PCR solution by mixing 2 µL of a qPCR mix solution (5× HOT FIREPoI® SolisGreen® qPCR mix) at a 5× concentration, 0.4 µL of a P3 primer solution at a 10 µM concentration, 0.4 µL of a P4 primer solution at a 10 µM concentration, 0.6 µL of a betaine solution at a 5 M concentration, 0.15 µL of dimethyl sulfoxide (DMSO), and 6.45 µL of ultrapure water, wherein the P3 primer has the sequence set forth in SEQ ID NO. 80; and the P4 primer has the sequence set forth in SEQ ID NO. 81;

(B6) amplifying the test sample and reading the result by performing the following steps from (a6) to (c6):

(a6) immersing the test sample by dipping the dipstick containing DNA of the pig blood sample into the tube of step (A6) for 5 seconds, removing excess solution by touching the tube wall, then sealing the tube to obtain a sample-loaded reaction tube;

(b6) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c6) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 4:
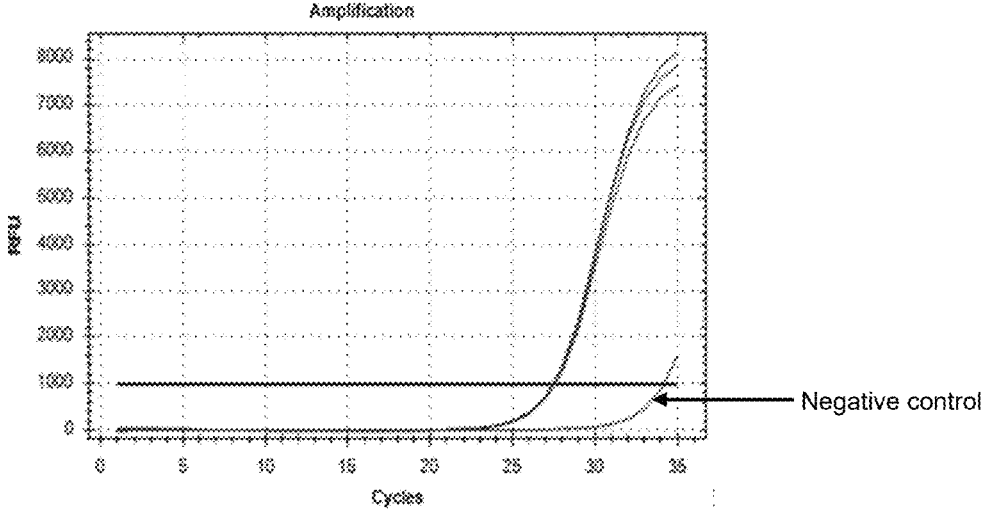
FIG. 4 shows the real-time PCR result for detecting the B646L gene of ASFV in the pig blood sample.
Figure 4:
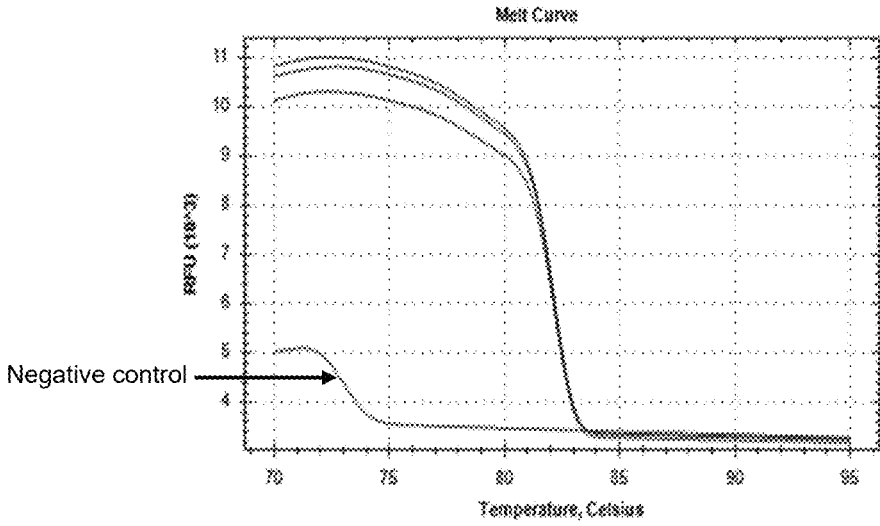
Figure 4:
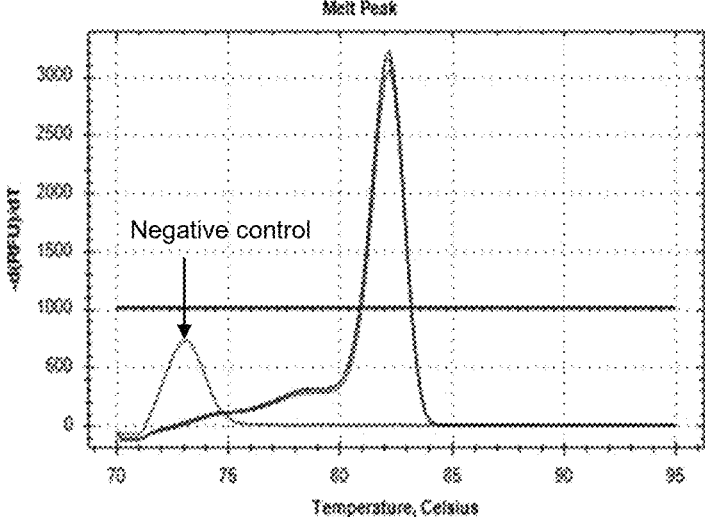
Figure 5:
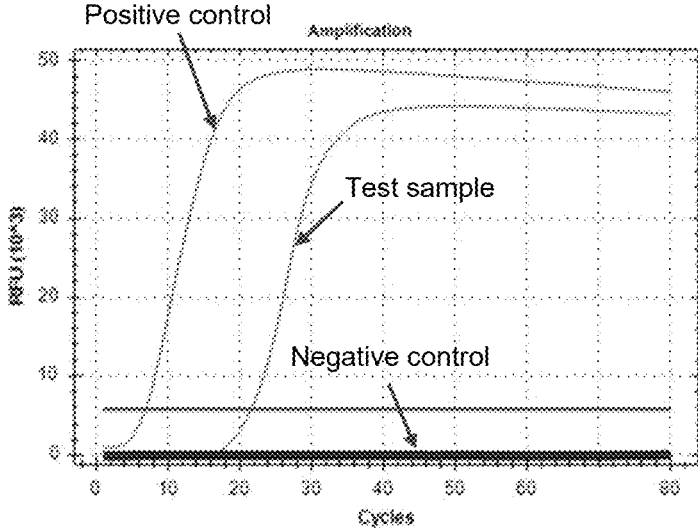
FIG. 5 shows the real-time LAMP result of for detecting the B646L gene of ASFV in the pig blood sample.
Figure 5:
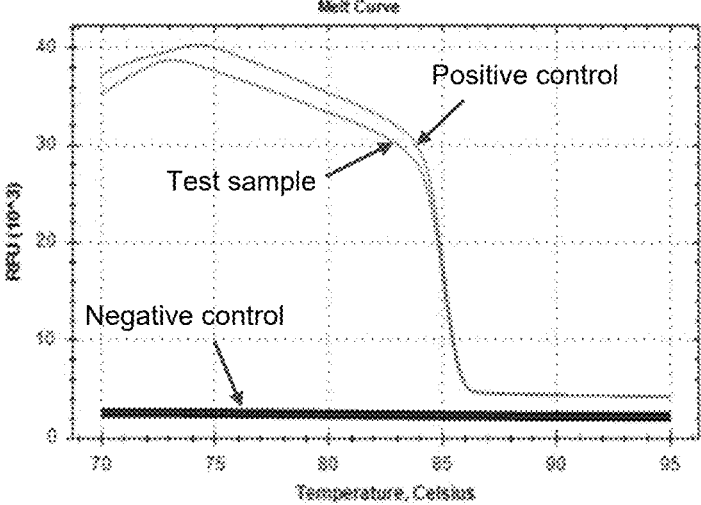
Figure 5:
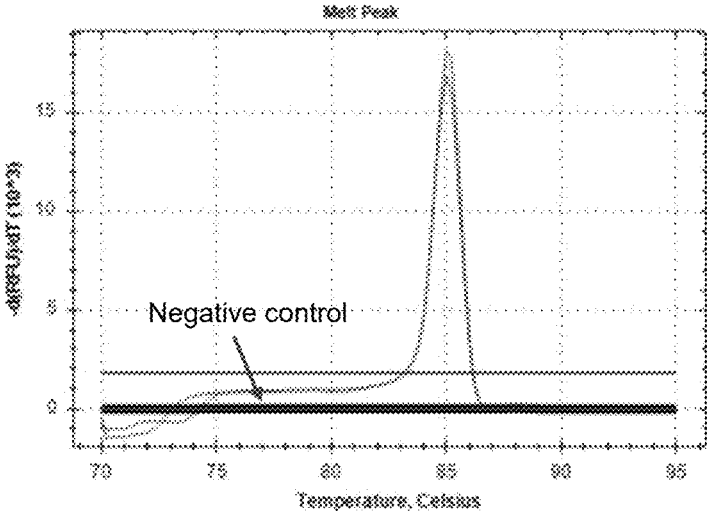

Method 100 is applied to detect the B646L gene of ASFV from DNA extracted from the pig blood sample by the real-time PCR. The primer set used for the real-time PCR comprises the P3 primer and the P4 primer, the sequences of which are referenced from King et al., 2003[4]. Reference to FIG. 4 shows the results of the real-time PCR assay for detecting the B646L gene of ASFV in the pig blood sample. The real-time PCR results display clear amplification curves in the amplification plot, confirming the presence of ASFV DNA in the tested samples. The melting curve and specific melting peak validate the specificity of the PCR product for the B646L gene of ASFV. No abnormal amplification signals were observed, indicating that the method 100 provided high-quality DNA suitable for real-time PCR analysis.

According to the preferred embodiment of the present invention, the test sample is a pig blood sample (*Sus scrofa*

*domesticus* Brisson) extracted to detect an African swine fever virus (ASFV) by the real-time LAMP, comprising the steps of:

(A7) preparing a tube containing a real-time LAMP solution by mixing 1 µL of a isothermal amplification buffer at a 10× concentration, 0.6 µL of MgSO₄, 1 µL of a LAMP-3 primer set solution at a 10× concentration, 0.4 µL of a DNA polymerase solution (Bst 2.0® DNA polymerase) at a 8 U/µL concentration, 0.6 µL of a guanidine hydrochloride solution at a 0.5 M concentration, 1.4 µL of dNTPs at a 40 mM concentration, and 0.5 µL of a fluorescent dye at a 20× concentration;

wherein the LAMP-3 primer set comprises:

a LAMP-3-F3 primer has the sequence set forth in SEQ ID NO. 82;

a LAMP-3-B3 primer has the sequence set forth in SEQ ID NO. 83;

a LAMP-3-FIP primer has the sequence set forth in SEQ ID NO. 84;

a LAMP-3-BIP primer has the sequence set forth in SEQ ID NO. 85;

a LAMP-3-LF primer has the sequence set forth in SEQ ID NO. 86; and a LAMP-3-LB primer has the sequence set forth in SEQ ID NO. 87;

(B7) amplifying the test sample and reading the result by performing the following steps from (a7) to (c7):

(a7) immersing the test sample by dipping the dipstick containing DNA of the pig blood sample into the tube of step (A7) for 5 seconds, removing excess solution by touching the tube wall, then sealing the tube to obtain a sample-loaded reaction tube;

(b7) placing the sample-loaded reaction tube in a real-time LAMP instrument and running the following thermal program:

step 1: 66° C. for 10 minutes; and step 2: 66° C. for 1 minute for 80 cycles; and step 3: performing a melting curve analysis by holding at 95° C. for 1 minute, then increasing from 70° C. to 95° C. at 0.2° C. every 2 seconds;

(c7) reading the result on the real-time LAMP instrument, wherein a positive result is indicated by the appearance of an amplification curve and a characteristic melting-curve peak; and a negative result is indicated by the absence of an amplification curve or a characteristic melting-curve peak.

Method 100 is applied to detect the B646L gene of African swine fever virus (ASFV) from DNA extracted from the pig blood sample (*Sus scrofa domesticus* Brisson) by the real-time LAMP. The LAMP-3 primer set is referenced from Tao et al., 2020[1]. FIG. refers to the image showing the results of the real-time LAMP for detecting the B646L gene of ASFV in the pig blood sample. The real-time LAMP results indicate a clear amplification signal for the positive sample, while the negative sample shows no amplification signal, confirming the specificity of the reaction. The amplification curve and melt curve analysis demonstrate that the reaction operates stably, making it suitable for detecting the B646L gene of ASFV.

According to the preferred embodiment of the present invention, the test sample is a pig tissue sample (*Sus scrofa domesticus* Brisson) extracted to detect ACTB and ACTG1 genes by the colorimetric LAMP using phenol red as an indicator to monitor the reaction, comprising the steps of:

(A8) preparing a DNA amplification solution by mixing a reaction solution with a LAMP-IC primer set solution at a ratio of 9:1 (v/v); wherein the reaction solution comprises a colorimetric LAMP master mix (WarmStart® colorimetric LAMP 2× master mix) at a 1× concentration, trehalose at a 0.45 M concentration, and guanidine hydrochloride (GuHCl) at a 0.04 M concentration;

the LAMP-IC primer set solution comprises a F31C primer solution at a 0.2 µM concentration, a B31C primer solution at a 0.2 µM concentration, a FIPIC primer solution at a 1.6 µM concentration, a BIPIC primer solution at a 1.6 µM concentration, a LFIC primer solution at a 0.4 µM concentration; and a LBIC primer solution at a 0.4 µM concentration; wherein the F31C primer has the sequence set forth in SEQ ID NO. 88;

the B31C primer has the sequence set forth in SEQ ID NO. 89;

the FIPIC primer has the sequence set forth in SEQ ID NO. 90;

the BIPIC primer has the sequence set forth in SEQ ID NO. 91;

the LFIC primer is selected from the sequences set forth in SEQ ID NOs. 92 or 93; and the LBIC primer is selected from the sequences set forth in SEQ ID NOs. 94 or 95;

(B8) amplifying the test sample and reading the result by performing the following steps from (a8) to (d8):

(a8) pipetting 5 µL of the DNA amplification solution into the bottom of a tube, then sealing the tube to obtain a tube containing the DNA amplification solution;

(b8) immersing the test sample by dipping the dipstick containing the DNA of the pig tissue sample into the tube from step (a8) for 5 seconds, removing excess solution by touching the tube wall, then sealing the tube to obtain a sample-loaded tube; wherein the sample-loaded tube appears red-pink;

(c8) incubating the sample-loaded tube in a heating device under the following thermal conditions: 25° C. for 2 minutes, followed by 65° C. for 40-50 minutes, to obtain a processed tube; and (d8) reading the result to detect the ACTB and ACTG1 genes, wherein:

a positive result is indicated when the processed tube changes to yellow; and a negative result is indicated when the processed tube remains red-pink.

Method 100 is applied to detect the ACTB and ACTG1 genes from DNA extracted from the pig tissue sample (*Sus scrofa domesticus* Brisson) by the colorimetric LAMP using phenol red as an indicator to monitor the reaction. The LAMP-IC primer set was custom-designed. Reference to Table 4 shows the results of applying method 100 using the pig tissue sample, with DNA amplification performed by the colorimetric LAMP.

TABLE 4

| Results of the colorimetric LAMP applying method 100 using the pig tissue sample | | | | |
| --- | --- | --- | --- | --- |
| Time | C_ | C_+ | Pig tissue sample 1 | Pig tissue sample 2 |
| Initial time | – | – | – | – |
| After 30 minutes | – | + | + | + | in which: C –: negative control;
C+: positive control;
(–): no reaction occurred;
(+): reaction occurred.

Based on Table 4, the results of the colorimetric LAMP show that after 30 minutes, the test samples (Pig tissue sample 1 and 2), along with the positive control (C_+), all exhibited a positive reaction (+), indicating the presence of the target DNA in the pig tissue samples. Meanwhile, the negative control (C_) showed no reaction, confirming the specificity of the experiment. This demonstrates that the colorimetric LAMP method can accurately detect the ACTB and ACTG1 genes in the pig tissue sample using method 100.

According to the preferred embodiment of the present invention, the test sample is a pig tissue sample (*Sus scrofa domesticus* Brisson) extracted to detect ACTB and ACTG1 genes by the PCR, comprising the steps of:

(A9) preparing a tube containing a PCR solution by mixing 2 µL of a qPCR mix solution (5× HOT FIRE-Pol® SolisGreen® qPCR mix) at a 5× concentration, 0.4 µL of a F31C primer solution at a 10 µM concentration, 0.4 µL of a B31C primer solution at a 10 µM concentration, 0.6 µL of a betaine solution at a 5 M concentration, 0.15 µL of dimethyl sulfoxide (DMSO), and 6.45 µL of ultrapure water; wherein the F31C primer has the sequence set forth in SEQ ID NO. 88; and the B31C primer has the sequence set forth in SEQ ID NO. 89;

(B9) amplifying the test sample and reading the result by performing the following steps from (a9) to (c9):

(a9) immersing the test sample by dipping the dipstick containing DNA of the pig tissue sample into the tube of step (A9) for 5 seconds, removing excess solution by touching the tube wall, then sealing the tube to obtain a sample-loaded reaction tube;

(b9) placing the sample-loaded reaction tube in a thermocycler and running the following program: step 1: 95° C. for 5 minutes; step 2: 35 cycles, each cycle comprising 94° C. for 15 seconds (denaturation), 56° C. for 30 seconds (annealing), and 72° C. for 30 seconds (extension); step 3: 72° C. for 5 minutes; and (c9) analyzing the amplification products by agarose gel electrophoresis using a 1.5% agarose gel in 1×TAE buffer at 100 V for 45 minutes, staining with a nucleic acid gel stain solution (GelRed® nucleic acid gel stain), and visualizing under UV illumination; wherein a positive result is indicated by the presence of a DNA band at approximately 257 base pairs, and a negative result is indicated by the absence of a DNA band at approximately 257 base pairs.

Figure 6:
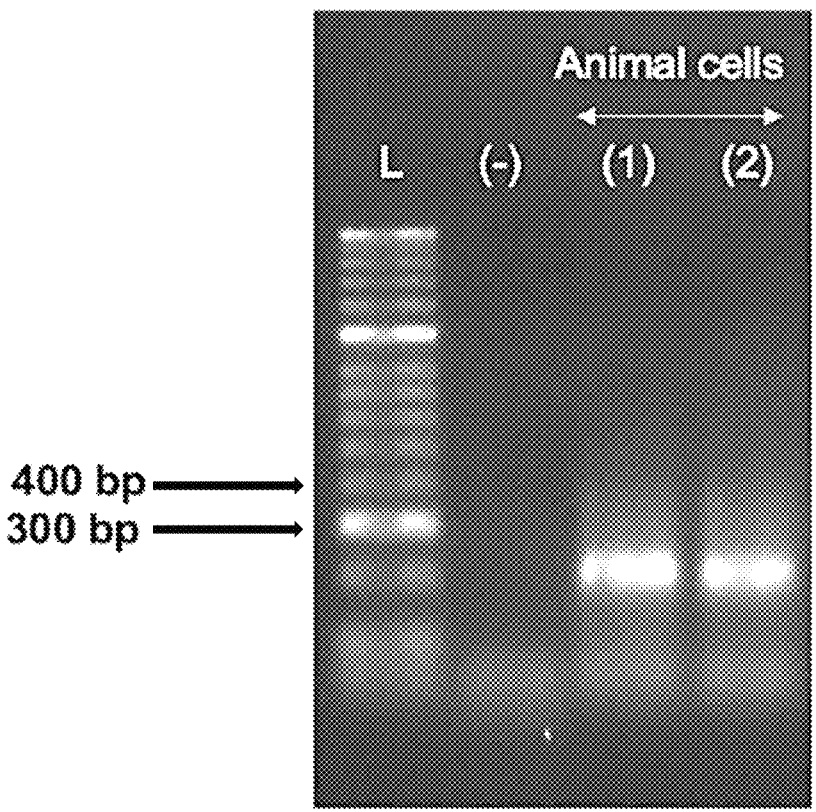
FIG. 6 shows the PCR result for detecting the ACTB and ACTG1 genes from the pig tissue samples.

Method 100 is applied to detect the actin gene from DNA extracted from the pig tissue sample (*Sus scrofa domesticus* Brisson) by the PCR. FIG. 6 presents an image of the PCR results for detecting the ACTB and ACTG1 genes from pig tissue samples. The two test samples, labeled (1) and (2), correspond to DNA extracted from pig tissue and exhibit clear amplification bands at approximately 257 base pairs, which matches the expected size of the ACTB and ACTG1 genes amplicon. The negative control, labeled (−), shows no amplification band, indicating no contamination or non-specific amplification.

According to the preferred embodiment of the present invention, the test sample is a pig tissue sample (*Sus scrofa domesticus* Brisson) extracted to detect ACTB and ACTG1 genes by the real-time PCR, comprising the steps of:

(A10) preparing a tube containing a real-time PCR solution by mixing 2 μL of a qPCR mix solution (5× HOT FIREPoI® SolisGreen® qPCR mix) at a 5× concentration, 0.4 μL of a F31C primer solution at a 10 μM concentration, 0.4 μL of a B31C primer solution at a 10 μM concentration, 0.6 μL of a betaine solution at a 5 M concentration, 0.15 μL of dimethyl sulfoxide (DMSO), and 6.45 μL of ultrapure water, wherein the F31C primer has the sequence set forth in SEQ ID NO. 88; and the B31C primer has the sequence set forth in SEQ ID NO. 89;

(B10) amplifying the test sample and reading the result by performing the following steps from (a10) to (c10):

(a10) immersing the test sample by dipping the dipstick containing DNA of the pig tissue sample into the tube of step (A10) for 5 seconds, removing excess solution by touching the tube wall, then sealing the tube to obtain a sample-loaded reaction tube;

(b10) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c10) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 7:
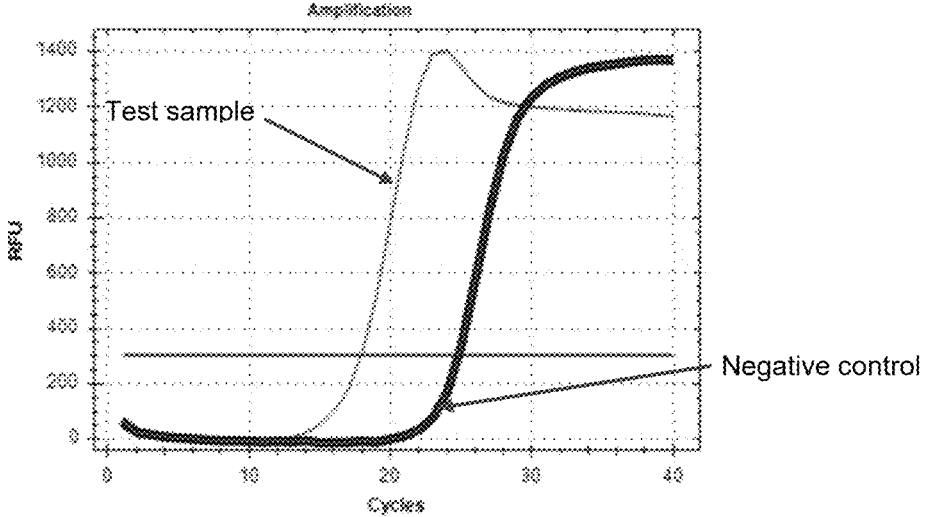
FIG. 7 shows the real-time PCR result of assay for detecting the ACTB and ACTG1 genes from the pig tissue sample.
Figure 7:
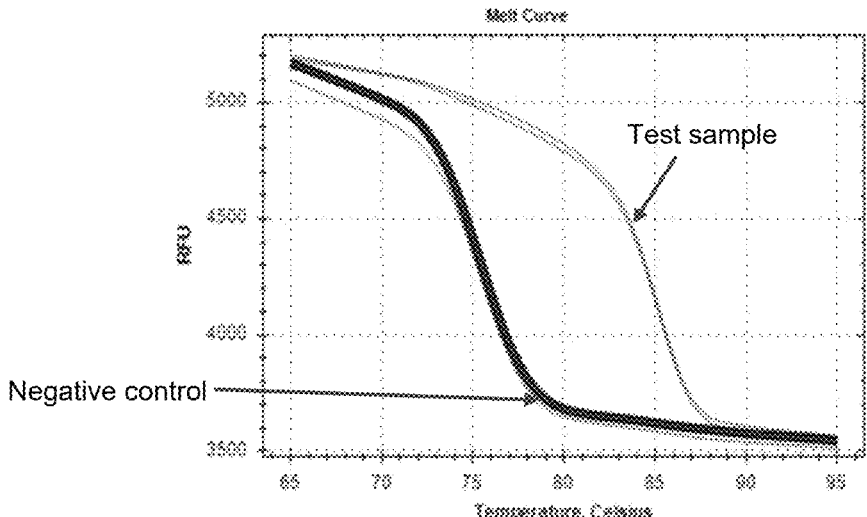
Figure 7:
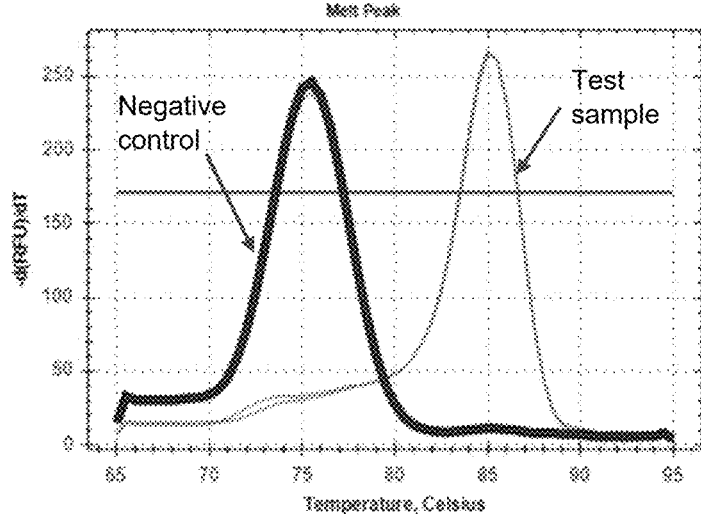

Method 100 is applied to detect the ACTB and ACTG1 genes from DNA extracted from the pig tissue sample (*Sus scrofa domesticus* Brisson) by the real-time PCR. Reference to FIG. 7 shows that positive reactions produce a clear amplification curve, with fluorescence (RFU) rising above baseline between cycles 16 and 20, while the no-template control remains flat. A subsequent melting-curve analysis yields a single peak at approximately 85° C. for each positive reaction, confirming the presence of the specific actin amplicon.

According to the preferred embodiment of the present invention, the test sample is a pig tissue sample (*Sus scrofa domesticus* Brisson) extracted to detect ACTB and ACTG1 genes by the real-time LAMP, comprising the steps of:

(A11) preparing a tube containing a real-time LAMP solution by mixing 1 μL of a isothermal amplification buffer at a 10× concentration, 0.6 μL of MgSO₄, 1 μL of a LAMP-IC primer set solution at a 10× concentration, 0.4 μL of a DNA polymerase solution (Bst 2.0® DNA polymerase) at a 8 U/μL concentration, 0.6 μL of a guanidine hydrochloride solution at a 0.5 M concentration, 1.4 μL of dNTPs at a 40 mM concentration; and 0.5 μL of a fluorescent dye at a 20× concentration;

wherein the LAMP-IC primer set solution comprises:

the F31C primer has the sequence set forth in SEQ ID NO. 88;

the B31C primer has the sequence set forth in SEQ ID NO. 89;

a FIPIC primer has the sequence set forth in SEQ ID NO. 90;

a BIPIC primer has the sequence set forth in SEQ ID NO. 91;

a LFIC primer selected from the sequences set forth in SEQ ID NOs. 92 and 93; and a LBIC primer selected from the sequences set forth in SEQ ID NOs. 94 and 95;

(B111) amplifying the test sample and reading the result by performing the following steps from (a11) to (c11):

(a11) immersing the test sample by dipping the dipstick containing DNA of the pig blood sample into the tube of step (A11) for 5 seconds, removing excess solution by touching the tube wall, then sealing the tube to obtain a sample-loaded reaction tube;

(b11) placing the sample-loaded reaction tube in a real-time LAMP instrument and running the following thermal program:

step 1: 66° C. for 10 minutes; and step 2: 66° C. for 1 minute for 80 cycles; and step 3: performing a melting curve analysis by holding at 95° C. for 1 minute, then increasing from 70° C. to 95° C. at 0.2° C. every 2 seconds;

(c11) reading the result on the real-time LAMP instrument, wherein a positive result is indicated by the appearance of an amplification curve and a characteristic melting-curve peak; and a negative result is indicated by the absence of an amplification curve or a characteristic melting-curve peak.

According to the preferred embodiment of the present invention, the test sample is a clinical specimen extracted to detect *Neisseria meningitidis* by the colorimetric LAMP using phenol red as an indicator to monitor the reaction, comprising the steps of:

(A12) preparing a DNA amplification solution by mixing a reaction solution with a LAMP-2 primer set solution at a ratio of 9:1 (v/v); wherein the reaction solution comprises a colorimetric LAMP master mix (WarmStart® colorimetric LAMP 2× master mix) at a 1× concentration, trehalose at a 0.45 M concentration, and guanidine hydrochloride (GuHCl) at a 0.04 M concentration;

the LAMP-2 primer set solution comprises a LAMP-2-F3 primer at a 0.2 μM concentration, a LAMP-2-B3 primer solution at a 0.2 μM concentration, a LAMP-2-FIP primer solution at a 1.6 μM concentration, a LAMP-2-BIP primer solution at a 1.6 μM concentration, and a LAMP-2-LF primer solution at a 0.4 μM concentration; wherein the LAMP-2-F3 primer has the sequence set forth in SEQ ID NO. 96;

the LAMP-2-B3 primer has the sequence set forth in SEQ ID NO. 97;

the LAMP-2-FIP primer has the sequence set forth in SEQ ID NO. 98;

the LAMP-2-BIP primer has the sequence set forth in SEQ ID NO. 99; and the LAMP-2-LF primer has the sequence set forth in SEQ ID NO. 100;

(B12) amplifying the test sample and reading the result by performing the following steps from (a12) to (d12):

(a12) pipetting 5 μL of the DNA amplification solution into the bottom of a tube, then sealing the tube to obtain a tube containing the DNA amplification solution;

(b12) immersing the test sample by dipping the dipstick containing the DNA of the clinical specimen into the tube from step (a12) for 5 seconds, removing excess solution by touching the tube wall, then sealing the tube to obtain a sample-loaded tube; wherein the sample-loaded tube appears red-pink;

(c12) incubating the sample-loaded tube in a heating device under the following thermal conditions: 25° C. for 2 minutes, followed by 65° C. for 50-60 minutes, to obtain a processed tube; and (d12) reading the result to detect *Neisseria meningitidis*, wherein:

a positive result is indicated when the processed tube changes to yellow; and a negative result is indicated when the processed tube remains red-pink.

Method 100 is applied to detect a metA gene of *Neisseria meningitidis* from DNA extracted from the clinical specimen (pharyngeal fluid sample) by the colorimetric LAMP using phenol red as an indicator to monitor the reaction. The LAMP-2 primer set was custom-designed. Reference to Table 5 shows the results of applying method 100 using the clinical specimen, with DNA amplification performed by the colorimetric LAMP.

TABLE 5

Results of the colorimetric LAMP applying method
100 using the clinical specimen

| Time | C_ | C_+ | Clinical specimen 1 | Clinical specimen 2 | Clinical specimen 3 |
|---|---|---|---|---|---|
| Initial time | – | – | – | – | – |
| After 60 minutes | – | + | + | + | + | in which: C –: negative control;
C+: positive control;
(–): no reaction occurred;
(+): reaction occurred.

As shown in Table 5, no color change is observed in the negative control (C_) or any clinical specimen at the initial time point, indicating that the assay mixture and dipstick transfer steps do not produce false-positive signals. After 60 minutes of incubation, the positive control (C_+) exhibits the expected color shift from red to yellow (denoted "+"), confirming that the phenol red indicator reliably reports successful LAMP amplification. Importantly, all three clinical specimens likewise show a positive reaction only after the 60-minute incubation, demonstrating that Method 100 enables robust detection of the metA target from pharyngeal fluid samples. The absence of amplification in the negative control and the consistent positive results for both the positive control and clinical specimens validate the specificity and sensitivity of the colorimetric LAMP protocol under the claimed conditions.

According to the preferred embodiment of the present invention, test sample is a clinical specimen extracted to detect *Neisseria meningitidis* by a PCR, comprising the steps of:

(A13) preparing a tube containing a PCR solution by mixing 2 μL of a qPCR mix solution (5× HOT FIREPoI® SolisGreen® qPCR mix) at a 5× concentration, 0.4 μL of a LAMP-2-F3 primer solution at a 10 μM concentration, 0.4 μL of a LAMP-2-B3 primer solution at a 10 μM concentration, 0.6 μL of a betaine solution at a 5 M concentration, 0.15 μL of dimethyl sulfoxide (DMSO), and 6.45 μL of ultrapure water; wherein the LAMP-2-F3 primer has the sequence set forth in SEQ ID NO. 96; and the LAMP-2-B3 primer has the sequence set forth in SEQ ID NO. 97;

(B13) amplifying the test sample and reading the result by performing the following steps from (a13) to (c13):

(a13) immersing the test sample by dipping the dipstick containing DNA of the clinical specimen into the tube of step (A13) for 5 seconds, removing excess solution by touching the tube wall, then sealing the tube to obtain a sample-loaded reaction tube;

(b13) placing the sample-loaded reaction tube in a thermocycler and running the following program:

step 1: 95° C. for 5 minutes;

step 2: 35 cycles, each cycle comprising 94° C. for 15 seconds (denaturation), 58° C. for 30 seconds (annealing), and 72° C. for 20 seconds (extension);

step 3: 72° C. for 5 minutes; and (c13) analyzing the amplification products by agarose gel electrophoresis using a 1.5% agarose gel in 1×TAE buffer at 100 V for 45 minutes, staining with a nucleic acid gel stain solution (GelRed® nucleic acid gel stain), and visualizing under UV illumination; wherein a positive result is indicated by the presence of a DNA band at approximately 227 base pairs, and a negative result is indicated by the absence of a DNA band at approximately 227 base pairs.

Figure 8:
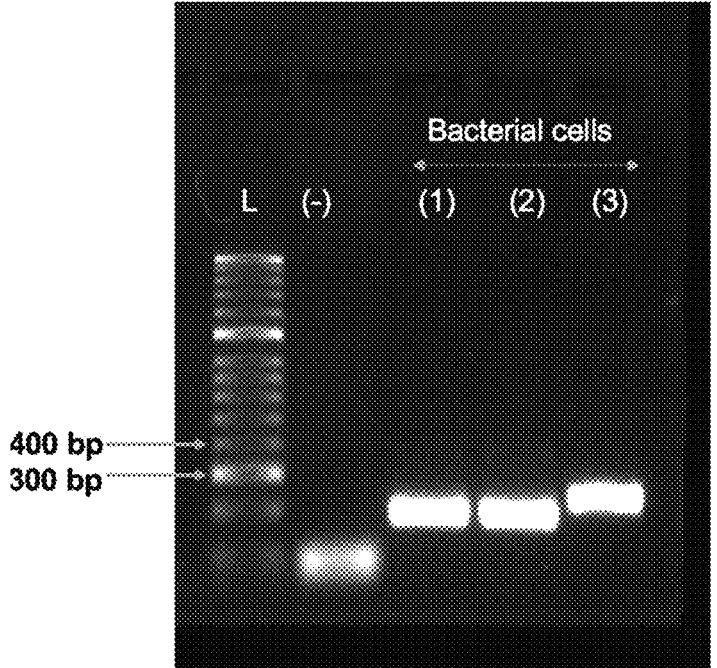
FIG. 8 shows the PCR result for detecting the metA gene of *Neisseria meningitidis*.

Method 100 is applied to detect a metA gene of *Neisseria meningitidis* from DNA extracted from the clinical specimen (pharyngeal fluid sample) by the PCR. Reference to FIG. 8 shows a clear 227 base pairs amplification product in lanes (1)-(3), corresponding to three independent pharyngeal fluid extracts. No band is observed in the negative control (–), confirming the absence of non-specific amplification.

According to the preferred embodiment of the present invention, the test sample is a clinical specimen extracted to detect *Neisseria meningitidis* by the real-time PCR, comprising the steps of:

(A14) preparing a tube containing a real-time PCR solution by mixing 2 μL of a qPCR mix solution (5× HOT FIREPoI® SolisGreen® qPCR mix) at a 5× concentration, 0.4 μL of a LAMP-2-F3 primer solution at a 10 μM concentration, 0.4 μL of a LAMP-2-B3 primer solution at a 10 μM concentration, 0.6 μL of a betaine solution at a 5 M concentration, 0.15 μL of dimethyl sulfoxide (DMSO), and 6.45 μL of ultrapure water, wherein the LAMP-2-F3 primer has the sequence set forth in SEQ ID NO. 96; and the LAMP-2-B3 primer has the sequence set forth in SEQ ID NO. 97;

(B14) amplifying the test sample and reading the result by performing the following steps from (a14) to (c14):

(a14) immersing the test sample by dipping the dipstick containing DNA of the clinical specimen into the tube of step (A14) for 5 seconds, removing excess solution by touching the tube wall, then sealing the tube to obtain a sample-loaded reaction tube;

(b14) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 58° C. for 30 seconds (annealing), and 72° C. for 20 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c14) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 9:
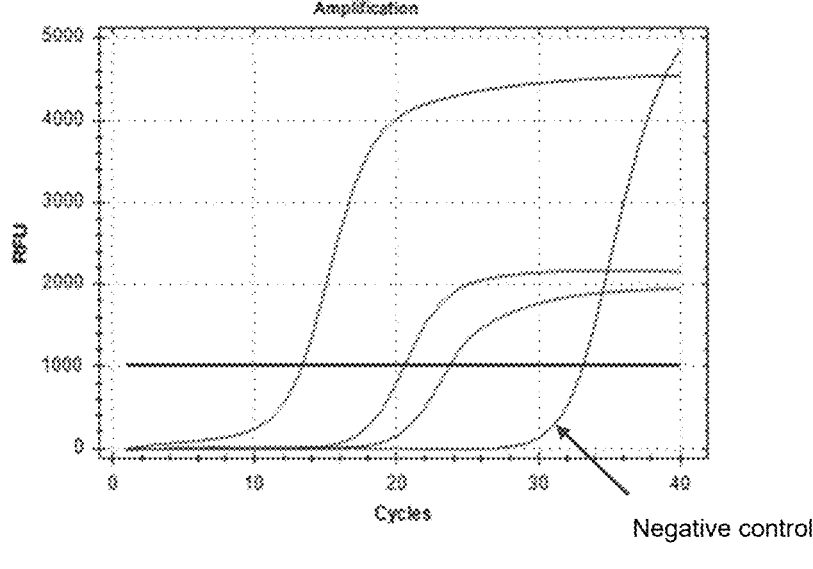
FIG. 9 shows the real-time PCR result for detecting the metA gene of *Neisseria meningitidis*.
Figure 9:
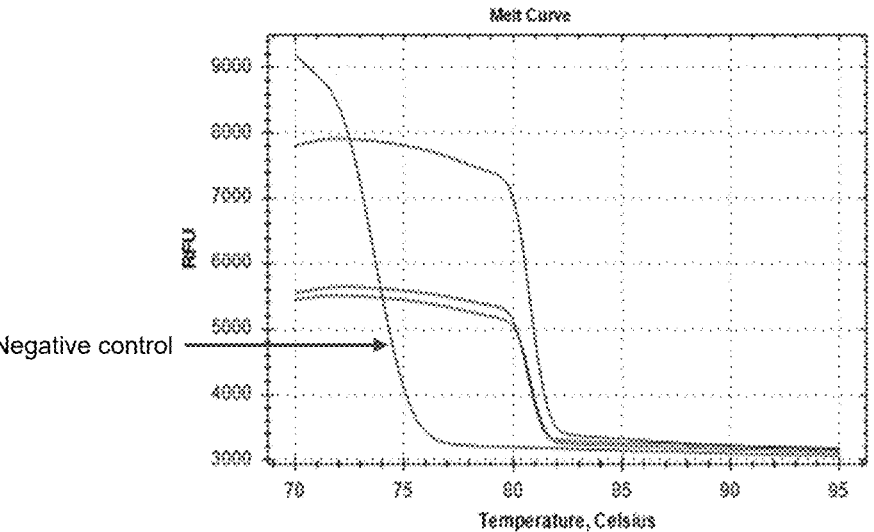
Figure 9:
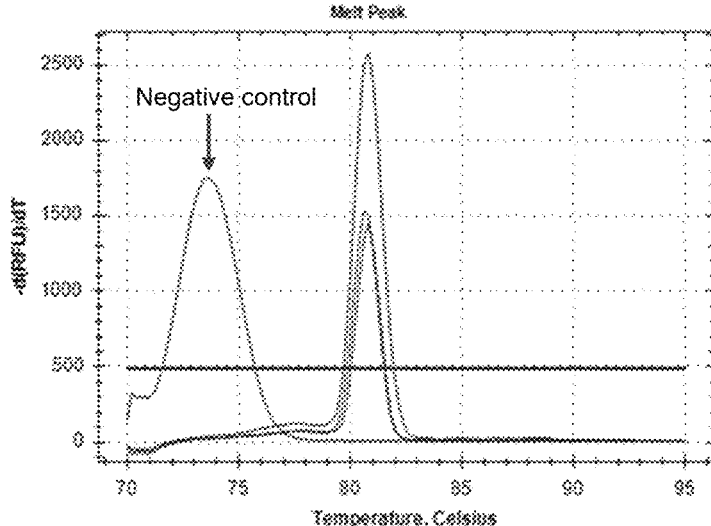

Method 100 is applied to detect a metA gene of *Neisseria meningitidis* from DNA extracted from the clinical specimen (pharyngeal fluid sample) by the real-time PCR. FIG. 9 shows the real-time PCR results obtained using DNA isolated from *Neisseria meningitidis* cells with the LAMP-2-F3 and LAMP-2-B3 primers.

According to the preferred embodiment of the present invention, the test sample is a fungal tissue sample extracted for molecular identification via PCR amplification of the target gene region, comprising the steps of:

(A15) preparing a tube containing a PCR solution by mixing 2 μL of a qPCR mix solution (5× HOT FIRE-Pol® SolisGreen® qPCR mix) at a 5× concentration, 0.4 μL of a first primer solution at a 10 μM concentration, 0.4 μL of a second primer solution at a 10 μM concentration, 0.6 μL of a betaine solution at a 5 M concentration, 0.15 μL of dimethyl sulfoxide (DMSO), and 6.45 μL of ultrapure water; wherein when the target gene region is ITS, the first primer has the sequence set forth in SEQ ID NO. 101 and the second primer has the sequence set forth in SEQ ID NO. 102;

when the target gene region is nrSSU, the first primer has the sequence set forth in SEQ ID NO. 103 and the second primer has the sequence set forth in SEQ ID NO. 104;

when the target gene region is nrLSU, the first primer has the sequence set forth in SEQ ID NO. 105 and the second primer has the sequence set forth in SEQ ID NO. 106;

when the target gene region is tubulin, the first primer has the sequence set forth in SEQ ID NO. 107 and the second primer has the sequence set forth in SEQ ID NO. 108;

(B15) amplifying the test sample and reading the result by performing the following steps from (a15) to (c15):

(a15) immersing the test sample by dipping the dipstick containing DNA of the fungal tissue sample into the tube of step (A15) for 5 seconds, removing excess solution by touching the tube wall, then sealing the tube to obtain a sample-loaded reaction tube;

(b15) placing the sample-loaded reaction tube in a thermocycler and running the following program:

wherein, when the target gene regions are ITS and tubulin, the thermal cycling program comprises:

step 1: 95° C. for 5 minutes;

step 2: 35 cycles, each cycle comprising 94° C. for 15 seconds (denaturation), 57° C. for 30 seconds (annealing), and 72° C. for 60 seconds (extension); and step 3: 72° C. for 5 minutes;

wherein, when the target gene region is nrSSU, the thermal cycling program comprises:

step 1: 95° C. for 5 minutes;

step 2: 35 cycles, each cycle comprising 94° C. for 15 seconds (denaturation), 43° C. for 30 seconds (annealing), and 72° C. for 60 seconds (extension); and step 3: 72° C. for 5 minutes;

wherein, when the target gene region is nrLSU, the thermal cycling program comprises:

step 1: 95° C. for 5 minutes;

step 2: 35 cycles, each cycle comprising 94° C. for 15 seconds (denaturation), 55° C. for 30 seconds (annealing), and 72° C. for 60 seconds (extension); and step 3: 72° C. for 5 minutes;

(c15) analyzing the amplification products by agarose gel electrophoresis using a 1.5% agarose gel in 1×TAE buffer at 100 V for 45 minutes, staining with nucleic acid gel stain solution (GelRed® nucleic acid gel stain), and visualizing under UV illumination; wherein a positive result is indicated by the presence of a DNA band at the specific expected size for each gene region, including:

471-1100 base pairs for the ITS region;

1102 base pairs for the nrSSU region;

938 base pairs for the nrLSU region;

860 base pairs for the tubulin region;

a negative result is indicated by the absence of any DNA band.

Figure 10:
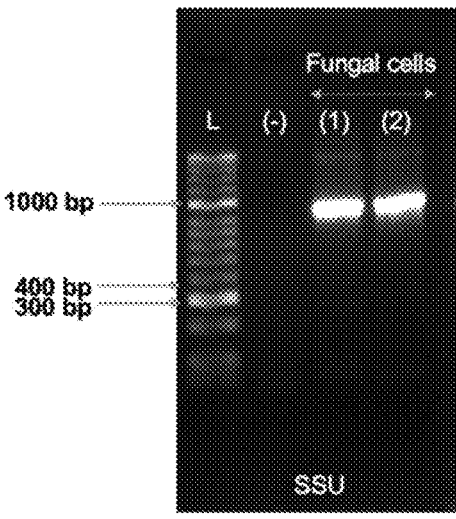
FIG. 10 shows the PCR result for detecting the target gene region of *Cordyceps militaris*.
Figure 10:
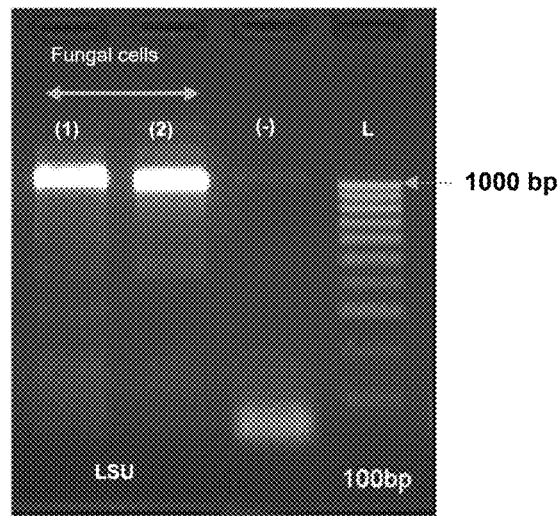
Figure 10:
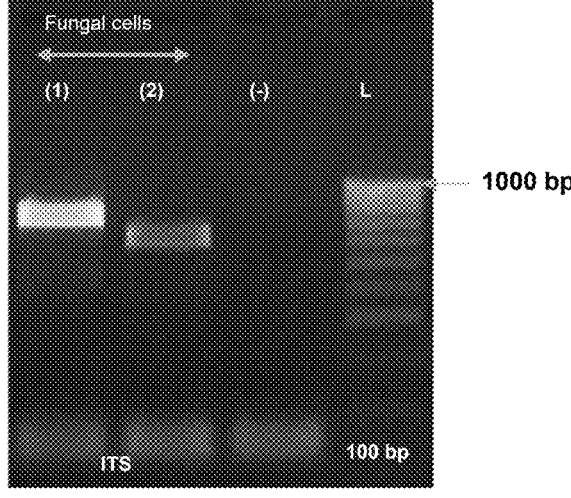

Method 100 is applied to detect the target gene region from DNA extracted from a fungal tissue sample (*Cordyceps militaris*) by the PCR. The primer sets for the ITS and nrSSU regions are referenced from White et al., 1990[5]; the nrLSU primers are referenced from Vilgalys & Sun, 1994[6]; and the β-tubulin primers are referenced from O'Donnell & Cigelnik, 1997[7]. Reference to FIG. 10 shows that, in the SSU panel, lanes (1) and (2) each produce a single band at 1102 base pairs, with no band in the negative control. In the LSU panel, lanes (1) and (2) each yield a discrete band at 938 base pairs, while the negative control remains blank. Finally, in the ITS panel, lanes (1) and (2) each display a distinct band at 471-1100 base pairs, with no product in the negative control.

According to the preferred embodiment of the present invention, the test sample is a fungal tissue sample extracted to detect a target gene region by the real-time PCR, comprising the steps of:

(A16) preparing a tube containing a real-time PCR solution by mixing 2 μL of a qPCR mix solution (5× HOT FIREPol® SolisGreen® qPCR mix) at a 5× concentration, 0.4 μL of a first primer solution at a 10 μM concentration, 0.4 μL of a second primer solution at a 10 μM concentration, 0.6 μL of a betaine solution at a 5 M concentration, 0.15 μL of dimethyl sulfoxide (DMSO), and 6.45 μL of ultrapure water; wherein when the target gene region is ITS, the first primer has the sequence set forth in SEQ ID NO. 101 and the second primer has the sequence set forth in SEQ ID NO. 102;

when the target gene region is nrSSU, the first primer has the sequence set forth in SEQ ID NO. 103 and the second primer has the sequence set forth in SEQ ID NO. 104;

when the target gene region is nrLSU, the first primer has the sequence set forth in SEQ ID NO. 105 and the second primer has the sequence set forth in SEQ ID NO. 106;

when the target gene region is tubulin, the first primer has the sequence set forth in SEQ ID NO. 107 and the second primer has the sequence set forth in SEQ ID NO. 108;

(B16) amplifying the test sample and reading the result by performing the following steps from (a16) to (c16):

(a16) immersing the test sample by dipping the dipstick containing DNA of the fungal tissue sample into the tube of step (A16) for 5 seconds, removing excess solution by touching the tube wall, then sealing the tube to obtain a sample-loaded reaction tube;

(b16) placing the sample-loaded reaction tube in a real-time PCR instrument and running the following thermal program:

wherein, when the target gene regions are ITS and tubulin, the thermal cycling program comprises:

step 1: 95° C. for 5 minutes;

step 2: 35 cycles, each cycle comprising 94° C. for 15 seconds (denaturation), 57° C. for 30 seconds (annealing), and 72° C. for 60 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

wherein, when the target gene region is nrSSU, the thermal cycling program comprises:

step 1: 95° C. for 5 minutes;

step 2: 35 cycles, each cycle comprising 94° C. for 15 seconds (denaturation), 43° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

wherein, when the target gene region is nrLSU, the thermal cycling program comprises:

step 1: 95° C. for 5 minutes;

step 2: 35 cycles, each cycle comprising 94° C. for 15 seconds (denaturation), 55° C. for 30 seconds (annealing), and 72° C. for 60 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

(c16) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 11:
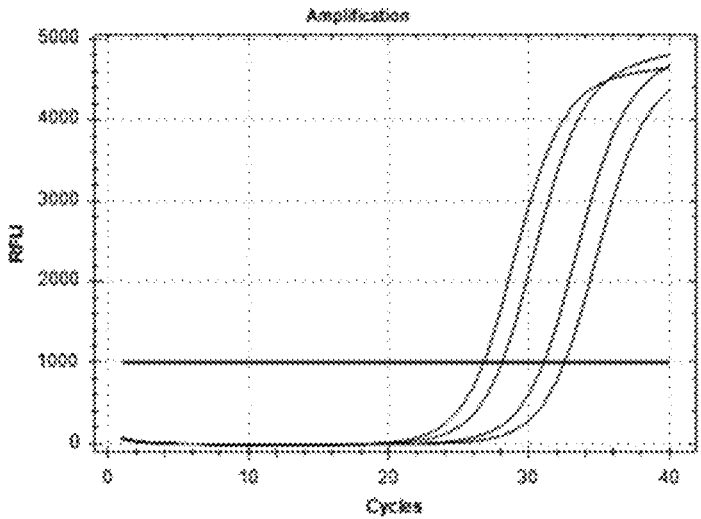
FIG. 11 shows the real-time PCR result for detecting the nrSSU region of *Cordyceps militaris*.
Figure 11:
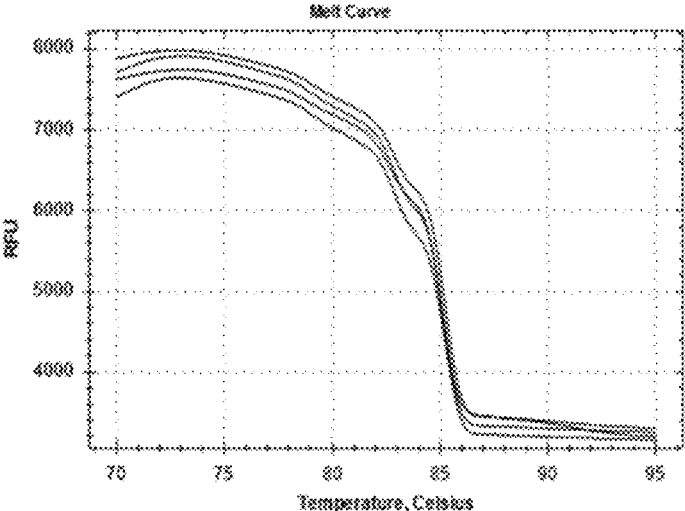
Figure 11:
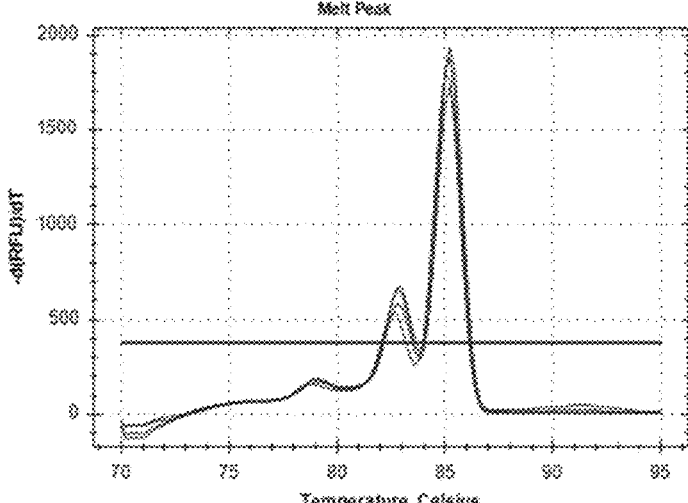
Figure 12:
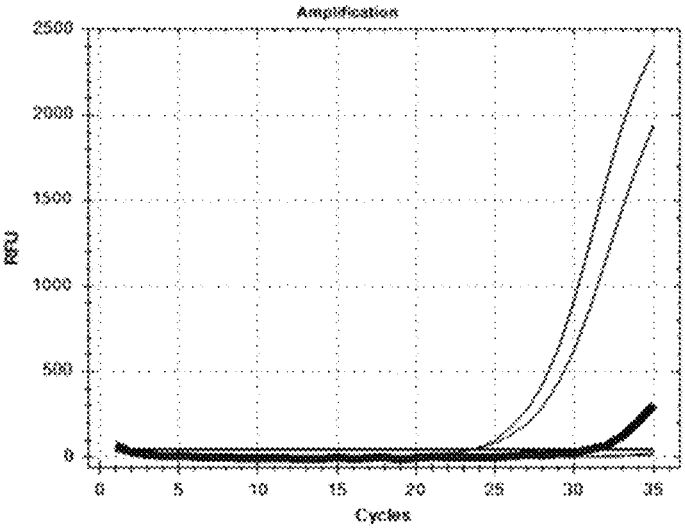
FIG. 12 shows the real-time PCR result for detecting the ITS region of *Cordyceps militaris*.
Figure 12:
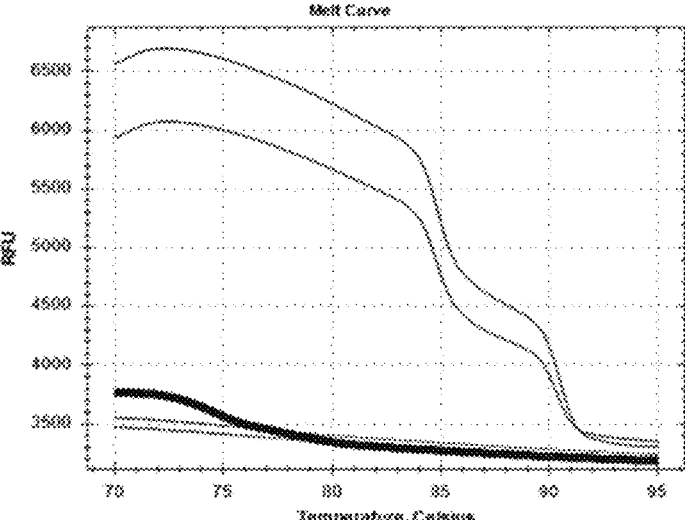
Figure 12:
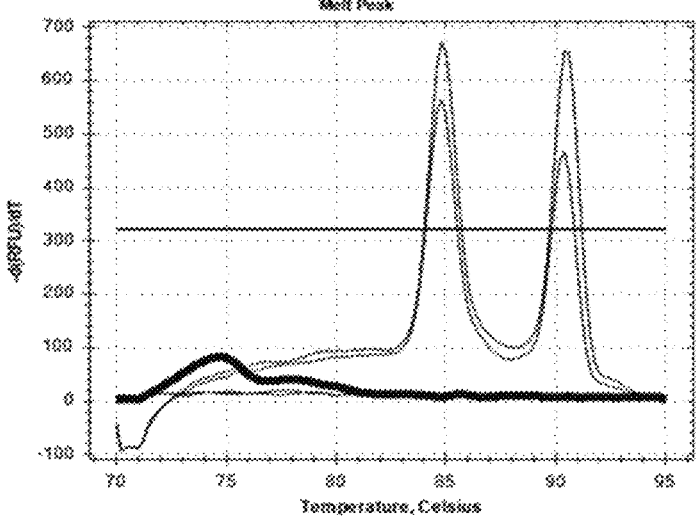
Figure 13:
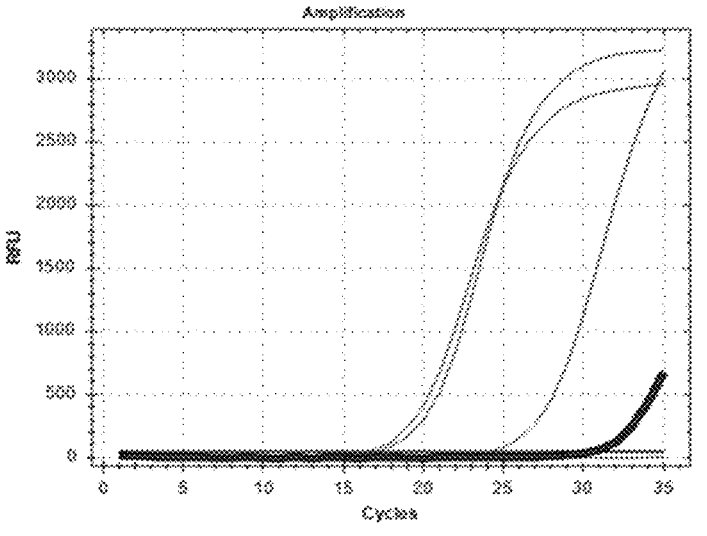
FIG. 13 shows the real-time PCR result for detecting the nrLSU region of *Cordyceps militaris*.
Figure 13:
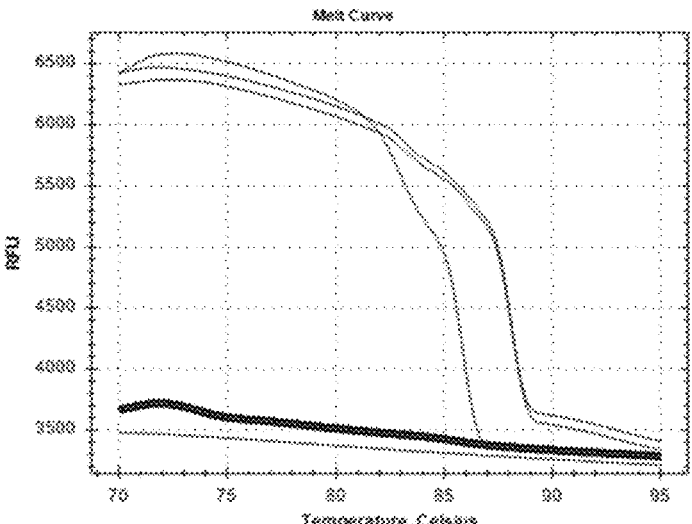
Figure 13:
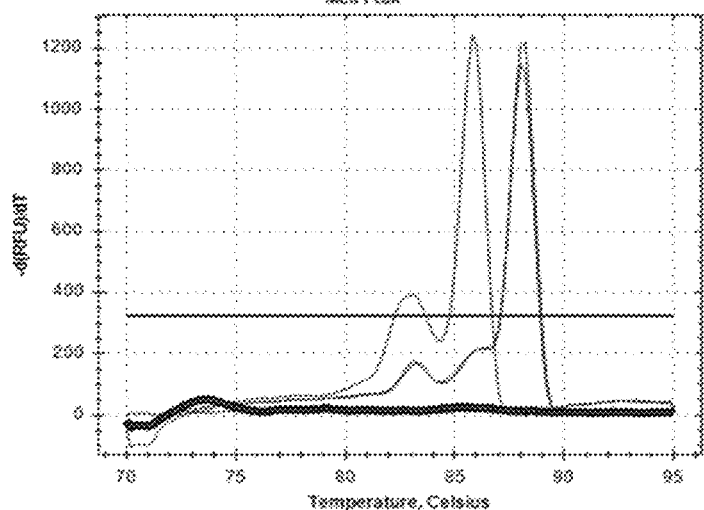
Figure 14:
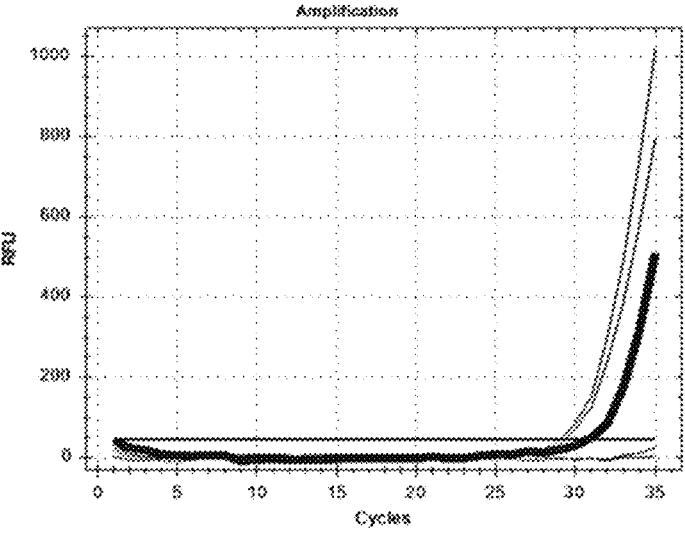
FIG. 14 shows the real-time PCR result for detecting the tubulin region of *Cordyceps militaris*.
Figure 14:
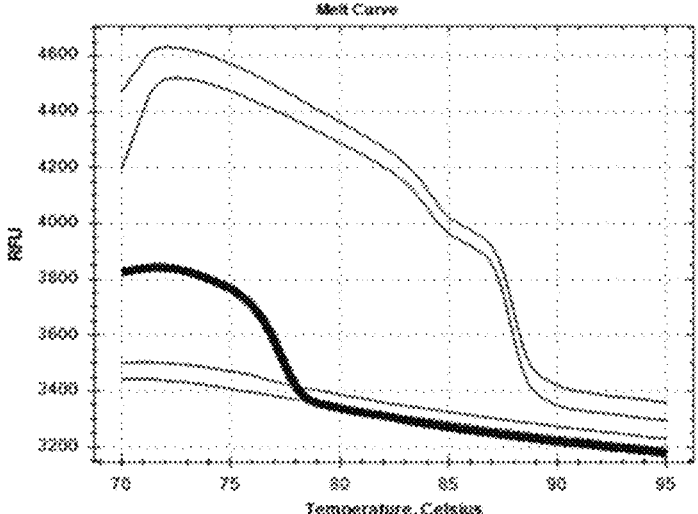
Figure 14:
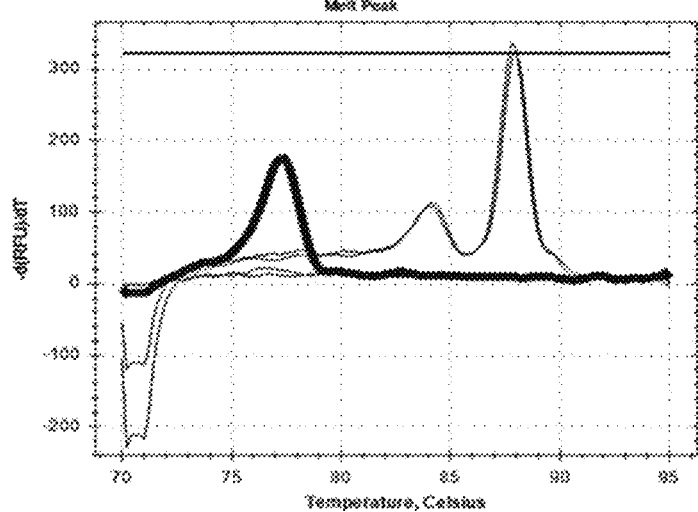

Method 100 is applied to detect the target gene region from DNA extracted from a fungal tissue sample (*Cordyceps militaris*) by the real-time PCR. Reference to FIG. 11 shows the amplification and melting-curve analysis of the nrSSU region, FIG. 12 shows the corresponding data for the ITS region, FIG. 13 shows the amplification and melting-curve analysis of the nrLSU region, and FIG. 14 shows the amplification and melting-curve analysis of the tubulin region.

According to the preferred embodiment of the present invention, the test sample is a swab sample containing human oral mucosal cells extracted to detect a beta actin gene by the PCR, comprising the steps of:

(A17) preparing a tube containing a PCR solution by mixing 2 μL of a qPCR mix solution (5× HOT FIRE-Pol® SolisGreen® qPCR mix) at a 5× concentration, 0.4 μL of a beta F primer solution at a 10 μM concentration, 0.4 μL of a beta R primer solution at a 10 μM concentration, 0.6 μL of a betaine solution at a 5 M concentration, 0.15 μL of dimethyl sulfoxide (DMSO), and 6.45 μL of ultrapure water; wherein the beta F primer has the sequence set forth in SEQ ID NO. 109; and the beta R primer has the sequence set forth in SEQ ID NO. 110;

(B17) amplifying the test sample and reading the result by performing the following steps from (a17) to (c17):

(a17) immersing the test sample by dipping the dipstick containing DNA of the swab sample into the tube of step (A17) for 5 seconds, removing excess solution by touching the tube wall, then sealing the tube to obtain a sample-loaded reaction tube;

(b17) placing the sample-loaded reaction tube in a thermocycler and running the following program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes; and (c17) analyzing the amplification products by agarose gel electrophoresis using a 1.5% agarose gel in 1×TAE buffer at 100 V for 45 minutes, staining with nucleic acid gel stain solution (GelRed® nucleic acid gel stain), and visualizing under UV illumination; wherein a positive result is indicated by the presence of a DNA band at approximately 319 base pairs, and a negative result is indicated by the absence of a DNA band at approximately 319 base pairs.

Figure 15:
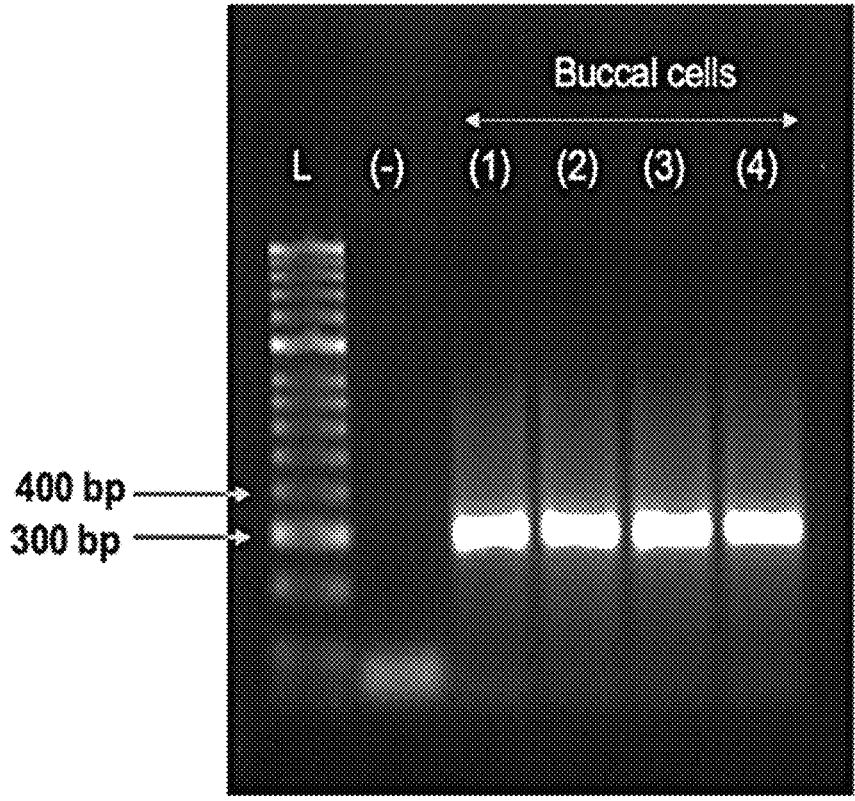
FIG. 15 shows the PCR result for detecting the beta actin gene from the buccal cell.

Method 100 is applied to detect the beta actin gene from DNA extracted from the swab sample (buccal cell) by the PCR. The primer set used for the PCR comprises the beta F primer and the beta R primer, the sequences of which are referenced from Yap et al., 2007[8]. Reference to FIG. 15 shows that, in the β-actin panel, lanes (1)-(4) each produce a single band at 319 base pairs, with no band in the negative control.

According to the preferred embodiment of the present invention, the test sample is a swab sample extracted to detect a beta actin gene by the real-time PCR, comprising the steps of:

(A18) preparing a tube containing a real-time PCR solution by mixing 2 μL of a qPCR mix solution (5× HOT FIREPoI® SolisGreen® qPCR mix) at a 5× concentration, 0.4 μL of a beta F primer solution at a 10 μM concentration, 0.4 μL of a beta R primer solution at a 10 μM concentration, 0.6 μL of a betaine solution at a 5 M concentration, 0.15 μL of dimethyl sulfoxide (DMSO), and 6.45 μL of ultrapure water, wherein the beta F primer has the sequence set forth in SEQ ID NO. 109; and the beta R primer has the sequence set forth in SEQ ID NO. 110;

(B18) amplifying the test sample and reading the result by performing the following steps from (a18) to (c18):

(a18) immersing the test sample by dipping the dipstick containing DNA of the swab sample into the tube of step (A18) for 5 seconds, removing excess solution by touching the tube wall, then sealing the tube to obtain a sample-loaded reaction tube;

(b18) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c18) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 16:
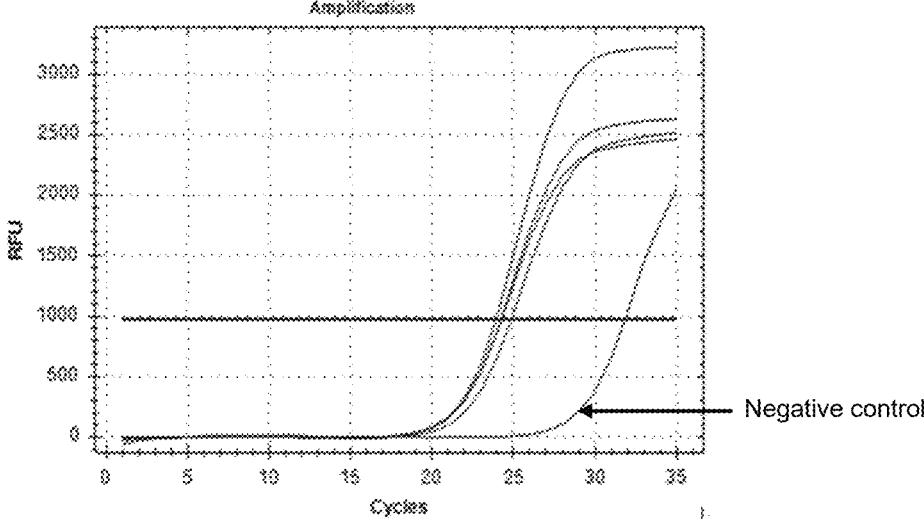
FIG. 16 shows the real-time PCR result for detecting the beta actin gene from the buccal cell.
Figure 16:
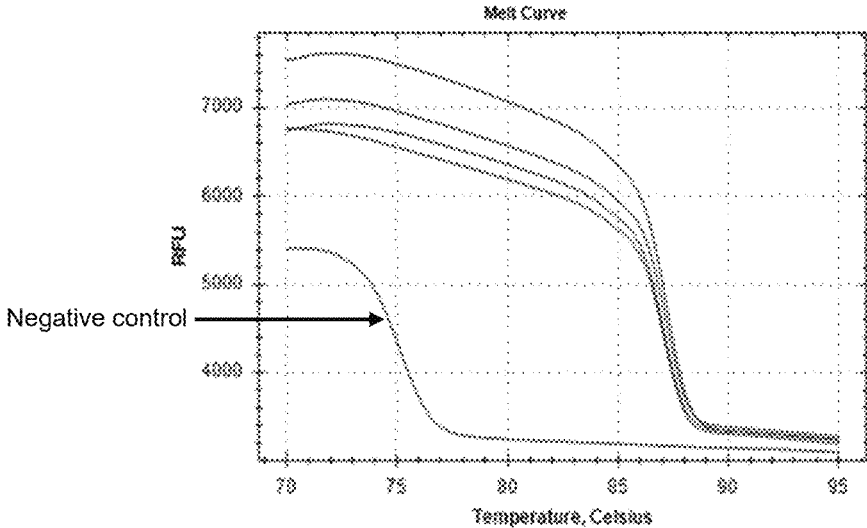
Figure 16:
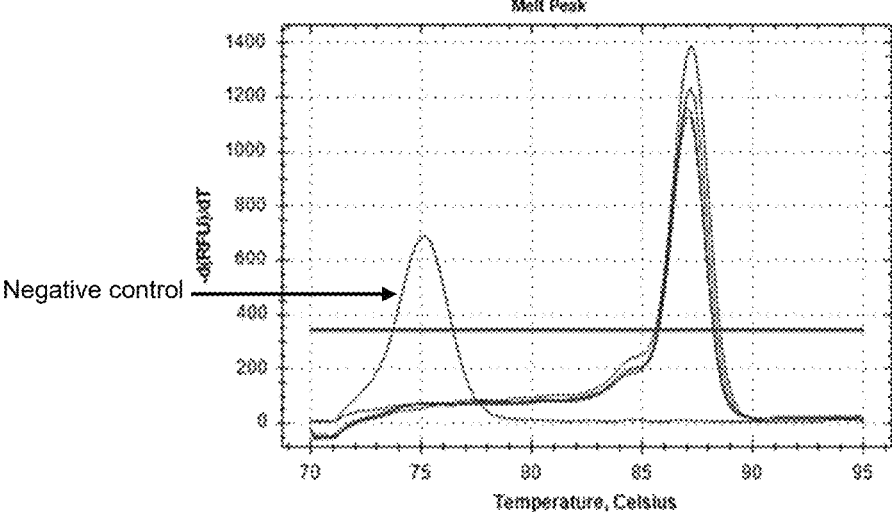

Method 100 is applied to detect the beta actin gene from DNA extracted from the swab sample (buccal cell) by the real-time PCR. Reference to FIG. 16 shows the amplification curves for the β-actin amplicon and the corresponding melt-curve analysis.

According to the preferred embodiment of the present invention, the test sample is a plant tissue sample extracted to detect a CLO gene by the PCR, comprising the steps of:

(A19) preparing a tube containing a PCR solution by mixing 2 μL of a qPCR mix solution (5× HOT FIRE-PoI® SolisGreen® qPCR mix) at a 5× concentration, 0.4 μL of a CLO-F primer solution at a 10 μM concentration, 0.4 μL of a CLO-R primer solution at a 10 μM concentration, 0.6 μL of a betaine solution at a 5 M concentration, 0.15 μL of dimethyl sulfoxide (DMSO), and 6.45 μL of ultrapure water; wherein the CLO-F primer has the sequence set forth in SEQ ID NO. 111; and the CLO-R primer has the sequence set forth in SEQ ID NO. 112;

(B19) amplifying the test sample and reading the result by performing the following steps from (a19) to (c19):

(a19) immersing the test sample by dipping the dipstick containing DNA of the plant tissue sample into the tube of step (A19) for 5 seconds, removing excess solution by touching the tube wall, then sealing the tube to obtain a sample-loaded reaction tube;

(b19) placing the sample-loaded reaction tube in a thermocycler and running the following program:

step 1: 95° C. for 5 minutes;

step 2: 35 cycles, each cycle comprising 94° C. for 15 seconds (denaturation), 60° C. for 30 seconds (annealing), and 72° C. for 60 seconds (extension);

step 3: 72° C. for 5 minutes; and (c19) analyzing the amplification products by agarose gel electrophoresis using a 1.5% agarose gel in 1×TAE buffer at 100 V for 45 minutes, staining with nucleic acid gel stain solution (GelRed® nucleic acid gel stain), and visualizing under UV illumination; wherein a positive result is indicated by the presence of a DNA band at approximately 422 base pairs, and a negative result is indicated by the absence of a DNA band at approximately 422 base pairs.

Figure 17:
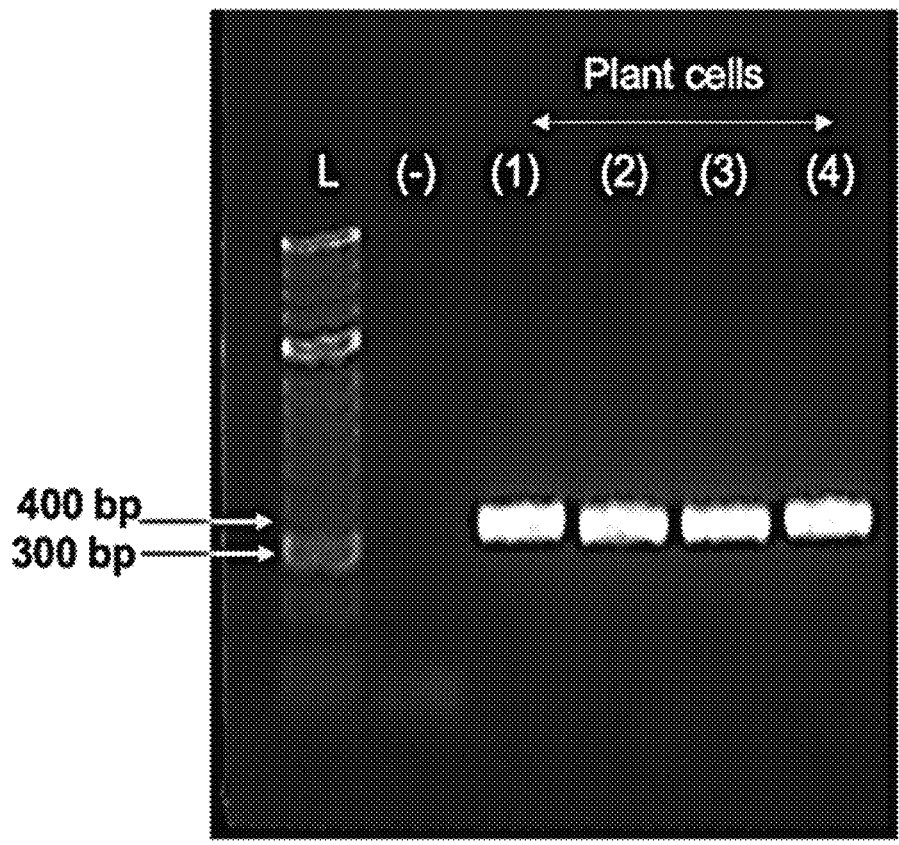
FIG. 17 shows the PCR result for detecting the CLO gene of *Ipomoea aquatica*.

Method 100 is applied to detect the CLO gene from DNA extracted from the plant tissue sample (Ipomoea aquatica) by the PCR. The primer set used for the PCR comprises the CLO-F primer and the CLO-R primer, the sequences of which are referenced from Taberlet et al., 1991[9]. Reference to FIG. 17 shows that, in the CLO panel, lanes (1)-(4) each yield a single amplicon at 422 base pairs corresponding to the target CLO fragment, while the negative control (−) exhibits no detectable band.

According to the preferred embodiment of the present invention, the test sample is a plant tissue sample extracted to detect a CLO gene by the real-time PCR, comprising the steps of:

(A20) preparing a tube containing a real-time PCR solution by mixing 2 μL of a qPCR mix solution (5× HOT FIREPoI® SolisGreen® qPCR mix) at a 5× concentration, 0.4 μL of a CLO-F primer solution at a 10 μM concentration, 0.4 μL of a CLO-R primer solution at a 10 μM concentration, 0.6 μL of a betaine solution at a 5 M concentration, 0.15 μL of dimethyl sulfoxide (DMSO), and 6.45 μL of ultrapure water, wherein the CLO-F primer has the sequence set forth in SEQ ID NO. 111; and the CLO-R primer has the sequence set forth in SEQ ID NO. 112;

(B20) amplifying the test sample and reading the result by performing the following steps from (a20) to (c20):

(a20) immersing the test sample by dipping the dipstick containing DNA of the plant tissue sample into the tube of step (A20) for 5 seconds, removing excess solution by touching the tube wall, then sealing the tube to obtain a sample-loaded reaction tube;

(b20) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 60° C. for 30 seconds (annealing), and 72° C. for 60 seconds (extension);

step 3: 72° C. for 5 minutes;

27 step 4: performing a melting curve analysis by holding at 95° C. for 1 minute, then increasing from 70° C. to 95° C. at 0.2° C. every 2 seconds; and (c20) reading the result on the real-time PCR instrument, wherein a positive result is indicated by the appearance of an amplification curve and a characteristic melting-curve peak; and a negative result is indicated by the absence of an amplification curve or a characteristic melting-curve peak.

Figure 18:
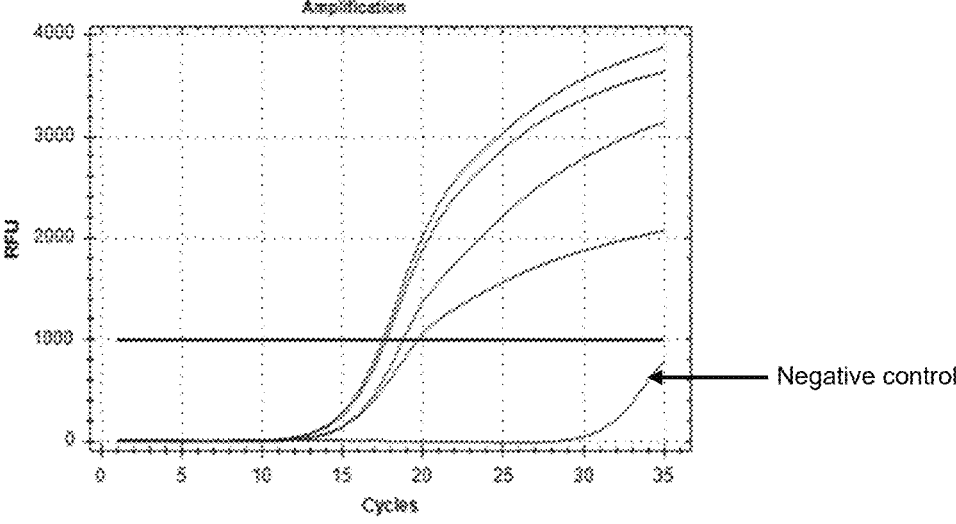
FIG. 18 shows the real-time PCR result for detecting the CLO gene of *Ipomoea aquatica*.
Figure 18:
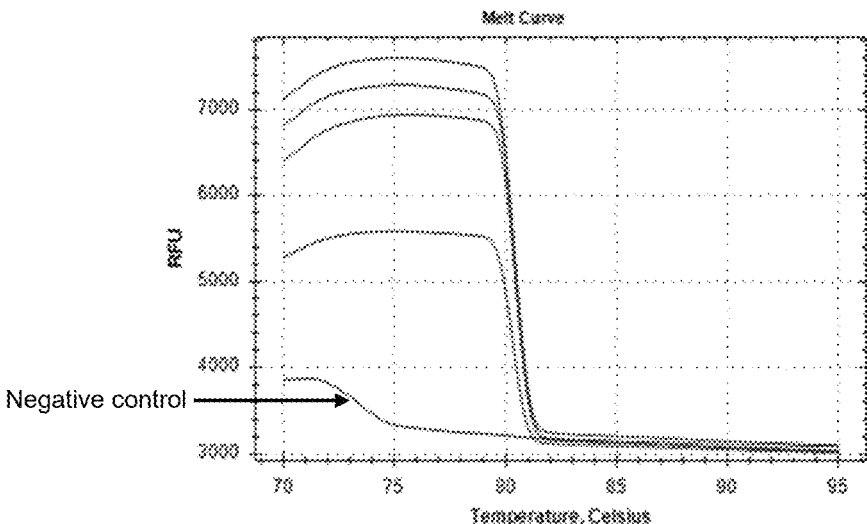
Figure 18:
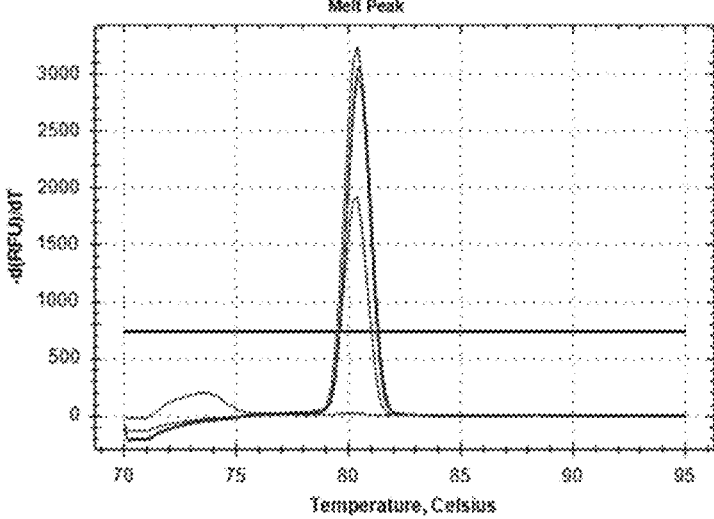

Method 100 is applied to detect the CLO gene from DNA extracted from the plant tissue sample (*Ipomoea aquatica*) by the real-time PCR. Reference to FIG. 18 shows the amplification curves for the CLO amplicon and the corresponding melt-curve analysis.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

REFERENCES

[1] Tao, D., Liu, J., Nie, X., Xu, B., Tran-Thi, T. N., Niu, L., . . . & Xie, S. (2020). Application of CRISPR-Cas12a enhanced fluorescence assay coupled with nucleic acid amplification for the sensitive detection of African swine fever virus. ACS Synthetic Biology, 9(9), 2339-2350;

[2] Bo, Y. A. N. G., Ma, Y., Wang, L., Cao, L., Luo, J., Wang, Y., . . . & Zheng, H. (2021). LAMP assay coupled with CRISPR/Cas12a system for portable detection of African swine fever virus. Authorea Preprints;

[3] Aguero, M., FernAndez, J., Romero, L., SAnchez Mascaraque, C., Arias, M., & SAnchez-Vizcaino, J. M. (2003). Highly sensitive PCR assay for routine diagnosis of African swine fever virus in clinical samples. Journal of clinical microbiology, 41(9), 4431-4434;

[4] King, D. P., Reid, S. M., Hutchings, G. H., Grierson, S. S., Wilkinson, P. J., Dixon, L. K., . . . & Drew, T. W. (2003). Development of a TaqMan® PCR assay with internal amplification control for the detection of African swine fever virus. Journal of virological methods, 107(1), 53-61;

[5] White, T. J., Bruns, T. D., Lee S., Taylor J. (1990). Amplification and direct sequencing of fungal ribosomal rna genes for phylogenetics. In Innis, M. A., Gelfand, D. H., Sninsky, J. J., White, T. J., (Eds.). Pcr protocols, a guide to methods and applications (pp. 315-322). San Diego: Academic Press;

[6] Vilgalys, R., Sun, B. L. (1994) Ancient and recent patterns of geographic speciation in the oyster mushroom *Pleurotus* revealed by phylogenetic analysis of ribosomal DNA sequences. Proc Natl Acad Sci USA, 91, 4599-4603;

[7] O'Donnell K, Cigelnik E (1997) Two divergent intragenomic rdna its 2 types within a monophyletic lineage of the fungus *Fusarium* are nonorthologous. Mol Phylogenet Evol 7, 103-116;

[8] Yap, Y. Y., Hassan, S., Chan, M., Choo, P. K., & Ravichandran, M. (2007). Epstein-Barr virus DNA detection in the diagnosis of nasopharyngeal carcinoma. Otolaryngology-Head and Neck Surgery, 136(6), 986-991;

[9] Taberlet, P., Gielly, L., Pautou, G. et al. (1991). Universal primers for amplification of three non-coding regions of chloroplast DNA. Plant Mol Biol, 17, 1105-1109.

What is claimed is:

1. A method for detecting a targeted nucleic acid from a deoxyribonucleic acid (DNA) sample extracted using a DNA extraction kit through DNA amplification testing comprising steps performed in the following specific order:

(i) preparing a DNA extraction kit and a test sample, wherein:

(A1) the DNA extraction kit comprising: a 1.5 mL tube containing from 230 to 250 μL of a lysis buffer, a 1.5 mL tube containing 200 μL of a wash buffer, and a dipstick;

wherein the lysis buffer has a pH of 8 and contains 1 mM Tris-HCl, 25 mM NaCl, 2.5 mM EDTA, and 0.05% SDS;

wherein the wash buffer has a pH of 8 and contains 0.75 mM Tris-HCl;

wherein the dipstick is prepared by performing steps from (a1) to (d1):

(a1) cutting a sheet of qualitative filter paper having an 11 μm pore size into paper strips each 56 mm long, 2 mm wide, and 0.18 mm thick;

(b1) applying an adhesive decal to one end of each paper strip of step (a1) to obtain a decal-treated strip comprising:

a first region 50 mm long, 2 mm wide, and 0.3 mm thick bearing the decal on both faces; and a second region 6 mm long, 2 mm wide, and 0.18 mm thick left undecorated;

(c1) immersing each decal-treated strip in molten paraffin wax for 10 seconds, then drying at 28° C. to 32° C. to obtain a paraffin-treated strip comprising three adjacent portions:

a handle portion corresponding to the decal-treated first region, 50 mm long, 2 mm wide, and 0.4-0.5 mm thick;

a fluid-barrier portion 3 mm long, 2 mm wide, and 0.2-0.3 mm thick; and a nucleic acid-capture portion corresponding to the undecorated second region, 3 mm long, 2 mm wide, and 0.18 mm thick;

(d1) irradiating both faces of each paraffin-treated strip of step (c1) with ultraviolet light for 15 minutes per side to obtain the dipstick;

(B1) the test sample is selected from the group comprising: a blood sample, a clinical specimen, a swab sample, an animal tissue sample, a plant tissue sample, a fungal tissue sample, a soil sample, and a water sample;

wherein the swab sample is prepared by:

inserting an end of a swab into a site on the subject's body containing biological fluid;

rotating the swab at the collection site for 10-20 seconds under light pressure so as to maximize adhesion of the sample onto the swab tip; and withdrawing the swab and air-drying it at 28° C. to 32° C. for 30 minutes to obtain the swab sample;

wherein the animal tissue sample is prepared by grinding 0.5 g of animal tissue for 10 minutes, adding 500 μL of the lysis buffer, and continuing to grind until a homogeneous mixture is formed;

wherein the plant tissue sample is prepared by grinding 0.5 g of plant tissue for 20 minutes, adding 500 μL of the lysis buffer, and continuing to grind until a homogeneous mixture is formed;

wherein the fungal tissue sample is prepared by grinding 0.5 g of fungal tissue for 10 minutes, adding 500 μL of the lysis buffer, and continuing to grind until a homogeneous mixture is formed;

(ii) adding an amount of the test sample to the 1.5 mL tube containing from 230 to 250 μL of the lysis buffer, shaking for 30 seconds, and incubating at 28° C. to 37° C. for 5 minutes to obtain a sample-containing tube;

wherein the blood sample is added in an amount of 20 μL;

wherein each of the clinical specimen, the animal tissue sample, the plant tissue sample, and the fungal tissue sample is added in an amount of 20 mg the homogeneous mixture;

wherein the swab sample is immersed into the lysis buffer;

(iii) shaking the sample-containing tube for 30 seconds, then immersing the dipstick into the sample-containing tube and holding it in place for 10-15 seconds to obtain a sample-loaded dipstick;

(iv) transferring the sample-loaded dipstick into the 1.5 mL tube containing 200 μL of the wash buffer, holding the dipstick in the wash buffer for 5 seconds, and then removing excess wash buffer from the dipstick by wiping the dipstick against the inner wall of the tube to obtain a dipstick containing the DNA of the test sample; and (v) amplifying the DNA from the dipstick containing the DNA of the test sample using a DNA amplification technique and reading the result to detect the targeted nucleic acid;

wherein the amplification technique is selected from the group consisting of: a polymerase chain reaction (PCR), a real-time PCR, a colorimetric loop-mediated isothermal amplification (LAMP), and a real-time LAMP.

2. The method of claim 1, wherein the DNA amplification technique is the colorimetric LAMP using phenol red as an indicator to monitor the reaction;

wherein the colorimetric LAMP is performed according to the following steps:

(A2) preparing a DNA amplification solution by mixing a reaction solution with a primer solution at a ratio of 9:1 (v/v), wherein the reaction solution comprises a colorimetric LAMP master mix at a 1× concentration, trehalose at a concentration of 0.45 M, and guanidine hydrochloride (GuHCl) at a concentration of 0.04 M; and (B2) amplifying the test sample and reading the result by performing the following steps from (a2) to (d2):

(a2) pipetting 5 μL of the DNA amplification solution into the bottom of a tube, then sealing the tube to obtain a tube containing the DNA amplification solution;

(b2) immersing the test sample by dipping the dipstick containing DNA of the test sample into the tube of step (a2) for 5 seconds, removing excess solution by touching the tube wall, then sealing the tube to obtain a sample-loaded tube; wherein the sample-loaded tube appears red-pink;

(c2) incubating the sample-loaded tube in a heating device under the following thermal conditions: 25° C. for 2 minutes, followed by 65° C. for 40-50 minutes, to obtain a processed tube; and (d2) reading the result to detect the targeted nucleic acid, wherein:

a positive result is indicated when the processed tube changes to yellow; and a negative result is indicated when the processed tube remains red-pink.

3. The method of claim 1, wherein the DNA amplification technique is the real-time LAMP is performed according to the following steps:

(A3) preparing a tube containing a real-time LAMP solution by mixing 1 μL of a isothermal amplification buffer at a 10× concentration, 0.6 μL of MgSO₄, 1 μL of a LAMP primer set solution at a 10× concentration, 0.4 μL of a DNA polymerase solution at a 8 U/μL concentration, 0.6 μL of a guanidine hydrochloride solution at a 0.5 M concentration, 1.4 μL of dNTPs at a 40 mM concentration, and 0.5 μL of a fluorescent dye at a 20× concentration;

(B3) amplifying the test sample and reading the result by performing the following steps from (a3) to (c3):

(a3) immersing the test sample by dipping the dipstick containing DNA of the test sample into the tube of step (A3) for 5 seconds, removing excess solution by touching the tube wall, then sealing the tube to obtain a sample-loaded reaction tube;

(b3) placing the sample-loaded reaction tube in a real-time LAMP instrument and running the following thermal program:

step 1: 66° C. for 10 minutes; and step 2: 66° C. for 1 minute for 80 cycles; and step 3: performing a melting curve analysis by holding at 95° C. for 1 minute, then increasing from 70° C. to 95° C. at 0.2° C. every 2 seconds;

(c3) reading the result on the real-time LAMP instrument, wherein a positive result is indicated by the appearance of an amplification curve and a characteristic melting-curve peak; and a negative result is indicated by the absence of an amplification curve or a characteristic melting-curve peak.

4. The method of claim 1, wherein the test sample is a pig blood sample (*Sus scrofa domesticus* Brisson) extracted to detect an African swine fever virus (ASFV) by the colorimetric LAMP using phenol red as an indicator to monitor the reaction, comprising the steps of:

(A4) preparing a DNA amplification solution by mixing a reaction solution with a LAMP-1 primer set solution at a ratio of 9:1 (v/v); wherein the reaction solution comprises a colorimetric LAMP 2× master mix at a 1× concentration, trehalose at a 0.45 M concentration, and guanidine hydrochloride (GuHCl) at a 0.04 M concentration;

the LAMP-1 primer set solution comprises a LAMP-1-F3 primer solution at a 0.2 μM concentration, a LAMP-1-B3 primer solution at a 0.2 μM concentration, a LAMP-1-FIP primer solution at a 1.6 μM concentration, a LAMP-1-BIP primer solution at a 1.6 μM concentration, a LAMP-1-LF primer solution at a 0.4 μM concentration, and a LAMP-1-LB primer solution at a 0.4 μM concentration; wherein the LAMP-1-F3 primer has the sequence set forth in SEQ ID NO. 1;

the LAMP-1-B3 primer is selected from the sequences set forth in SEQ ID NOs. 2 to 5;

the LAMP-1-FIP primer is selected from the sequences set forth in SEQ ID NOs. 6 to 21;

the LAMP-1-BIP primer is selected from the sequences set forth in SEQ ID NOs. 22 to 53;

the LAMP-1-LF primer is selected from the sequences set forth in SEQ ID NOs. 54 to 69; and the LAMP-1-LB primer is selected from the sequences set forth in SEQ ID NOs. 70 to 77;

(B4) amplifying the test sample and reading the result by performing the following steps from (a4) to (d4):

(a4) pipetting 5 μL of the DNA amplification solution into the bottom of a tube, then sealing the tube to obtain a tube containing the DNA amplification solution;

(b4) immersing the test sample by dipping the dipstick containing the DNA of the pig blood sample into the tube from step (a4) for 5 seconds, removing excess solution by touching the tube wall, then sealing the tube to obtain a sample-loaded tube; wherein the sample-loaded tube appears red-pink;

(c4) incubating the sample-loaded tube in a heating device under the following thermal conditions: 25° C. for 2 minutes, followed by 65° C. for 40-50 minutes, to obtain a processed tube; and (d4) reading the result to detect the target virus, wherein:

a positive result is indicated when the processed tube changes to yellow; and a negative result is indicated when the processed tube remains red-pink.

5. The method of claim 1, wherein the test sample is a pig blood sample (*Sus scrofa domesticus* Brisson) extracted to detect an African swine fever virus (ASFV) by the PCR, comprising the steps of:

(A5) preparing a tube containing a PCR solution by mixing 2 μL of a qPCR mix solution at a 5× concentration, 0.4 μL of a P1 primer solution at a 10 μM concentration, 0.4 μL of a P2 primer solution at a 10 μM concentration, 0.6 μL of a betaine solution at a 5 M concentration, 0.15 μL of dimethyl sulfoxide (DMSO), and 6.45 μL of ultrapure water; wherein the P1 primer has the sequence set forth in SEQ ID NO. 78; and the P2 primer has the sequence set forth in SEQ ID NO. 79;

(B5) amplifying the test sample and reading the result by performing the following steps from (a5) to (c5):

(a5) immersing the test sample by dipping the dipstick containing DNA of the pig blood sample into the tube of step (A5) for 5 seconds, removing excess solution by touching the tube wall, then sealing the tube to obtain a sample-loaded reaction tube;

(b5) placing the sample-loaded reaction tube in a thermocycler and running the following program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes; and (c5) analyzing the amplification products by agarose gel electrophoresis using a 1.5% agarose gel in 1×TAE buffer at 100 V for 45 minutes, staining with a nucleic acid gel stain solution, and visualizing under UV illumination; wherein a positive result is indicated by the presence of a DNA band at approximately 257 base pairs, and a negative result is indicated by the absence of a DNA band at approximately 257 base pairs.

6. The method of claim 1, wherein the test sample is a pig blood sample (*Sus scrofa domesticus* Brisson) extracted to detect an African swine fever virus (ASFV) by the real-time PCR, comprising the steps of:

(A6) preparing a tube containing a real-time PCR solution by mixing 2 μL of a qPCR mix solution at a 5× concentration, 0.4 μL of a P3 primer solution at a 10 μM concentration, 0.4 μL of a P4 primer solution at a 10 μM concentration, 0.6 μL of a betaine solution at a 5 M concentration, 0.15 μL of dimethyl sulfoxide (DMSO), and 6.45 μL of ultrapure water, wherein the P3 primer has the sequence set forth in SEQ ID NO. 80; and the P4 primer has the sequence set forth in SEQ ID NO. 81;

(B6) amplifying the test sample and reading the result by performing the following steps from (a6) to (c6):

(a6) immersing the test sample by dipping the dipstick containing DNA of the pig blood sample into the tube of step (A6) for 5 seconds, removing excess solution by touching the tube wall, then sealing the tube to obtain a sample-loaded reaction tube;

(b6) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c6) reading the result on the real-time PCR instrument, wherein a positive result is indicated by the appearance of an amplification curve and a characteristic melting-curve peak; and a negative result is indicated by the absence of an amplification curve or a characteristic melting-curve peak.

7. The method of claim 1, wherein the test sample is a pig blood sample (*Sus scrofa domesticus* Brisson) extracted to detect an African swine fever virus (ASFV) by the real-time LAMP, comprising the steps of:

(A7) preparing a tube containing a real-time LAMP solution by mixing 1 μL of a isothermal amplification buffer at a 10× concentration, 0.6 μL of MgSO$_4$, 1 μL of a LAMP-3 primer set solution at a 10× concentration, 0.4 μL of a DNA polymerase solution at a 8 U/μL concentration, 0.6 μL of a guanidine hydrochloride solution at a 0.5 M concentration, 1.4 μL of dNTPs at a 40 mM concentration, and 0.5 μL of a fluorescent dye at a 20× concentration;

wherein the LAMP-3 primer set comprises:

a LAMP-3-F3 primer has the sequence set forth in SEQ ID NO. 82;

a LAMP-3-B3 primer has the sequence set forth in SEQ ID NO. 83;

a LAMP-3-FIP primer has the sequence set forth in SEQ ID NO. 84;

a LAMP-3-BIP primer has the sequence set forth in SEQ ID NO. 85;

a LAMP-3-LF primer has the sequence set forth in SEQ ID NO. 86; and a LAMP-3-LB primer has the sequence set forth in SEQ ID NO. 87;

(B7) amplifying the test sample and reading the result by performing the following steps from (a7) to (c7):

(a7) immersing the test sample by dipping the dipstick containing DNA of the pig blood sample into the tube of step (A7) for 5 seconds, removing excess solution by touching the tube wall, then sealing the tube to obtain a sample-loaded reaction tube;

(b7) placing the sample-loaded reaction tube in a real-time LAMP instrument and running the following thermal program:

step 1: 66° C. for 10 minutes; and step 2: 66° C. for 1 minute for 80 cycles; and step 3: performing a melting curve analysis by holding at 95° C. for 1 minute, then increasing from 70° C. to 95° C. at 0.2° C. every 2 seconds;

(c7) reading the result on the real-time LAMP instrument, wherein a positive result is indicated by the appearance of an amplification curve and a characteristic melting-curve peak; and a negative result is indicated by the absence of an amplification curve or a characteristic melting-curve peak.

8. The method of claim 1, wherein the test sample is a pig tissue sample (*Sus scrofa domesticus* Brisson) extracted to detect ACTB and ACTG1 genes by the colorimetric LAMP using phenol red as an indicator to monitor the reaction, comprising the steps of:

(A8) preparing a DNA amplification solution by mixing a reaction solution with a LAMP-IC primer set solution at a ratio of 9:1 (v/v); wherein the reaction solution comprises a colorimetric LAMP master mix at a 1× concentration, trehalose at a 0.45 M concentration, and guanidine hydrochloride (GuHCl) at a 0.04 M concentration;

the LAMP-IC primer set solution comprises a F31C primer solution at a 0.2 μM concentration, a B31C primer solution at a 0.2 μM concentration, a FIPIC primer solution at a 1.6 μM concentration, a BIPIC primer solution at a 1.6 μM concentration, a LFIC primer solution at a 0.4 μM concentration; and a LBIC primer solution at a 0.4 μM concentration; wherein the F31C primer has the sequence set forth in SEQ ID NO. 88;

the B31C primer has the sequence set forth in SEQ ID NO. 89;

the FIPIC primer has the sequence set forth in SEQ ID NO. 90;

the BIPIC primer has the sequence set forth in SEQ ID NO. 91;

the LFIC primer is selected from the sequences set forth in SEQ ID NOs. 92 or 93; and the LBIC primer is selected from the sequences set forth in SEQ ID NOs. 94 or 95;

(B8) amplifying the test sample and reading the result by performing the following steps from (a8) to (d8):

(a8) pipetting 5 μL of the DNA amplification solution into the bottom of a tube, then sealing the tube to obtain a tube containing the DNA amplification solution;

(b8) immersing the test sample by dipping the dipstick containing the DNA of the pig tissue sample into the tube from step (a8) for 5 seconds, removing excess solution by touching the tube wall, then sealing the tube to obtain a sample-loaded tube; wherein the sample-loaded tube appears red-pink;

(c8) incubating the sample-loaded tube in a heating device under the following thermal conditions: 25° C. for 2 minutes, followed by 65° C. for 40-50 minutes, to obtain a processed tube; and (d8) reading the result to detect the ACTB and ACTG1 genes, wherein:
a positive result is indicated when the processed tube changes to yellow; and
a negative result is indicated when the processed tube remains red-pink.

9. The method of claim 1, wherein the test sample is a pig tissue sample (*Sus scrofa domesticus* Brisson) extracted to detect ACTB and ACTG1 genes by the PCR, comprising the steps of:

(A9) preparing a tube containing a PCR solution by mixing 2 μL of a qPCR mix solution at a 5× concentration, 0.4 μL of a F31C primer solution at a 10 μM concentration, 0.4 μL of a B31C primer solution at a 10 μM concentration, 0.6 μL of a betaine solution at a 5 M concentration, 0.15 μL of dimethyl sulfoxide (DMSO), and 6.45 μL of ultrapure water; wherein
the F31C primer has the sequence set forth in SEQ ID NO. 88; and
the B31C primer has the sequence set forth in SEQ ID NO. 89;

(B9) amplifying the test sample and reading the result by performing the following steps from (a9) to (c9):

(a9) immersing the test sample by dipping the dipstick containing DNA of the pig tissue sample into the tube of step (A9) for 5 seconds, removing excess solution by touching the tube wall, then sealing the tube to obtain a sample-loaded reaction tube;

(b9) placing the sample-loaded reaction tube in a thermocycler and running the following program:
step 1: 95° C. for 5 minutes;
step 2: 35 cycles, each cycle comprising 94° C. for 15 seconds (denaturation), 56° C. for 30 seconds (annealing), and 72° C. for 30 seconds (extension);
step 3: 72° C. for 5 minutes; and (c9) analyzing the amplification products by agarose gel electrophoresis using a 1.5% agarose gel in 1×TAE buffer at 100 V for 45 minutes, staining with a nucleic acid gel stain solution, and visualizing under UV illumination; wherein
a positive result is indicated by the presence of a DNA band at approximately 257 base pairs, and
a negative result is indicated by the absence of a DNA band at approximately 257 base pairs.

10. The method of claim 1, wherein the test sample is a pig tissue sample (*Sus scrofa domesticus* Brisson) extracted to detect ACTB and ACTG1 genes by the real-time PCR, comprising the steps of:

(A10) preparing a tube containing a real-time PCR solution by mixing 2 μL of a qPCR mix solution at a 5× concentration, 0.4 μL of a F31C primer solution at a 10 μM concentration, 0.4 μL of a B31C primer solution at a 10 μM concentration, 0.6 μL of a betaine solution at a 5 M concentration, 0.15 μL of dimethyl sulfoxide (DMSO), and 6.45 μL of ultrapure water, wherein
the F31C primer has the sequence set forth in SEQ ID NO. 88; and
the B31C primer has the sequence set forth in SEQ ID NO. 89;

(B10) amplifying the test sample and reading the result by performing the following steps from (a10) to (c10):

(a10) immersing the test sample by dipping the dipstick containing DNA of the pig tissue sample into the tube of step (A10) for 5 seconds, removing excess solution by touching the tube wall, then sealing the tube to obtain a sample-loaded reaction tube;

(b10) placing the sample-loaded reaction tube in a real-time PCR instrument and running the following thermal program:
step 1: 95° C. for 5 minutes;
step 2: 35 cycles, each cycle comprising 94° C. for 15 seconds (denaturation), 56° C. for 30 seconds (annealing), and 72° C. for 30 seconds (extension);
step 3: 72° C. for 5 minutes;
step 4: performing a melting curve analysis by holding at 95° C. for 1 minute, then increasing from 70° C. to 95° C. at 0.2° C. every 2 seconds; and (c10) reading the result on the real-time PCR instrument, wherein
a positive result is indicated by the appearance of an amplification curve and a characteristic melting-curve peak; and
a negative result is indicated by the absence of an amplification curve or a characteristic melting-curve peak.

11. The method of claim 1, wherein the test sample is a pig tissue sample (*Sus scrofa domesticus* Brisson) extracted to detect ACTB and ACTG1 genes by the real-time LAMP, comprising the steps of:

(A11) preparing a tube containing a real-time LAMP solution by mixing 1 μL of a isothermal amplification buffer at a 10× concentration, 0.6 μL of $MgSO_4$, 1 μL of a LAMP-IC primer set solution at a 10× concentration, 0.4 μL of a DNA polymerase solution at a 8 U/μL concentration, 0.6 μL of a guanidine hydrochloride solution at a 0.5 M concentration, 1.4 μL of dNTPs at a 40 mM concentration; and 0.5 μL of a fluorescent dye at a 20× concentration;
wherein the LAMP-IC primer set solution comprises:
the F31C primer has the sequence set forth in SEQ ID NO. 88;
the B31C primer has the sequence set forth in SEQ ID NO. 89;
a FIPIC primer has the sequence set forth in SEQ ID NO. 90;
a BIPIC primer has the sequence set forth in SEQ ID NO. 91;
a LFIC primer selected from the sequences set forth in SEQ ID NOs. 92 and 93; and
a LBIC primer selected from the sequences set forth in SEQ ID NOs. 94 and 95;

(B111) amplifying the test sample and reading the result by performing the following steps from (a11) to (c11):

(a11) immersing the test sample by dipping the dipstick containing DNA of the pig blood sample into the tube of step (A11) for 5 seconds, removing excess solution by touching the tube wall, then sealing the tube to obtain a sample-loaded reaction tube;

(b11) placing the sample-loaded reaction tube in a real-time LAMP instrument and running the following thermal program:
step 1: 66° C. for 10 minutes; and
step 2: 66° C. for 1 minute for 80 cycles; and
step 3: performing a melting curve analysis by holding at 95° C. for 1 minute, then increasing from 70° C. to 95° C. at 0.2° C. every 2 seconds;

(c11) reading the result on the real-time LAMP instrument, wherein
    a positive result is indicated by the appearance of an amplification curve and a characteristic melting-curve peak; and
    a negative result is indicated by the absence of an amplification curve or a characteristic melting-curve peak.

12. The method of claim 1, wherein the test sample is a clinical specimen extracted to detect *Neisseria meningitidis* by the colorimetric LAMP using phenol red as an indicator to monitor the reaction, comprising the steps of:
    (A12) preparing a DNA amplification solution by mixing a reaction solution with a LAMP-2 primer set solution at a ratio of 9:1 (v/v); wherein
        the reaction solution comprises a colorimetric LAMP master mix at a 1× concentration, trehalose at a 0.45 M concentration, and guanidine hydrochloride (GuHCl) at a 0.04 M concentration;
        the LAMP-2 primer set solution comprises a LAMP-2-F3 primer at a 0.2 μM concentration, a LAMP-2-B3 primer solution at a 0.2 μM concentration, a LAMP-2-FIP primer solution at a 1.6 μM concentration, a LAMP-2-BIP primer solution at a 1.6 μM concentration, and a LAMP-2-LF primer solution at a 0.4 μM concentration; wherein
        the LAMP-2-F3 primer has the sequence set forth in SEQ ID NO. 96;
        the LAMP-2-B3 primer has the sequence set forth in SEQ ID NO. 97;
        the LAMP-2-FIP primer has the sequence set forth in SEQ ID NO. 98;
        the LAMP-2-BIP primer has the sequence set forth in SEQ ID NO. 99; and
        the LAMP-2-LF primer has the sequence set forth in SEQ ID NO. 100;
    (B12) amplifying the test sample and reading the result by performing the following steps from (a12) to (d12):
        (a12) pipetting 5 μL of the DNA amplification solution into the bottom of a tube, then sealing the tube to obtain a tube containing the DNA amplification solution;
        (b12) immersing the test sample by dipping the dipstick containing the DNA of the clinical specimen into the tube from step (a12) for 5 seconds, removing excess solution by touching the tube wall, then sealing the tube to obtain a sample-loaded tube; wherein the sample-loaded tube appears red-pink;
        (c12) incubating the sample-loaded tube in a heating device under the following thermal conditions: 25° C. for 2 minutes, followed by 65° C. for 50-60 minutes, to obtain a processed tube; and
        (d12) reading the result to detect *Neisseria meningitidis*, wherein:
            a positive result is indicated when the processed tube changes to yellow; and
            a negative result is indicated when the processed tube remains red-pink.

13. The method of claim 1, wherein the test sample is a clinical specimen extracted to detect *Neisseria meningitidis* by a PCR, comprising the steps of:
    (A13) preparing a tube containing a PCR solution by mixing 2 μL of a qPCR mix solution at a 5× concentration, 0.4 μL of a LAMP-2-F3 primer solution at a 10 μM concentration, 0.4 μL of a LAMP-2-B3 primer solution at a 10 μM concentration, 0.6 μL of a betaine solution at a 5 M concentration, 0.15 μL of dimethyl sulfoxide (DMSO), and 6.45 μL of ultrapure water; wherein
        the LAMP-2-F3 primer has the sequence set forth in SEQ ID NO. 96; and
        the LAMP-2-B3 primer has the sequence set forth in SEQ ID NO. 97;
    (B13) amplifying the test sample and reading the result by performing the following steps from (a13) to (c13):
        (a13) immersing the test sample by dipping the dipstick containing DNA of the clinical specimen into the tube of step (A13) for 5 seconds, removing excess solution by touching the tube wall, then sealing the tube to obtain a sample-loaded reaction tube;
        (b13) placing the sample-loaded reaction tube in a thermocycler and running the following program:
        step 1: 95° C. for 5 minutes;
        step 2: 35 cycles, each cycle comprising 94° C. for 15 seconds (denaturation), 58° C. for 30 seconds (annealing), and 72° C. for 20 seconds (extension);
        step 3: 72° C. for 5 minutes; and
        (c13) analyzing the amplification products by agarose gel electrophoresis using a 1.5% agarose gel in 1×TAE buffer at 100 V for 45 minutes, staining with a nucleic acid gel stain solution, and visualizing under UV illumination; wherein
        a positive result is indicated by the presence of a DNA band at approximately 227 base pairs, and
        a negative result is indicated by the absence of a DNA band at approximately 227 base pairs.

14. The method of claim 1, wherein the test sample is a clinical specimen extracted to detect *Neisseria meningitidis* by the real-time PCR, comprising the steps of:
    (A14) preparing a tube containing a real-time PCR solution by mixing 2 μL of a qPCR mix solution at a 5× concentration, 0.4 μL of a LAMP-2-F3 primer solution at a 10 μM concentration, 0.4 μL of a LAMP-2-B3 primer solution at a 10 μM concentration, 0.6 μL of a betaine solution at a 5 M concentration, 0.15 μL of dimethyl sulfoxide (DMSO), and 6.45 μL of ultrapure water, wherein
        the LAMP-2-F3 primer has the sequence set forth in SEQ ID NO. 96; and
        the LAMP-2-B3 primer has the sequence set forth in SEQ ID NO. 97;
    (B14) amplifying the test sample and reading the result by performing the following steps from (a14) to (c14):
        (a14) immersing the test sample by dipping the dipstick containing DNA of the clinical specimen into the tube of step (A14) for 5 seconds, removing excess solution by touching the tube wall, then sealing the tube to obtain a sample-loaded reaction tube;
        (b14) placing the sample-loaded reaction tube in a real-time PCR instrument and running the following thermal program:
        step 1: 95° C. for 5 minutes;
        step 2: 35 cycles, each cycle comprising 94° C. for 15 seconds (denaturation), 58° C. for 30 seconds (annealing), and 72° C. for 20 seconds (extension);
        step 3: 72° C. for 5 minutes;
        step 4: performing a melting curve analysis by holding at 95° C. for 1 minute, then increasing from 70° C. to 95° C. at 0.2° C. every 2 seconds; and (c14) reading the result on the real-time PCR instrument, wherein a positive result is indicated by the appearance of an amplification curve and a characteristic melting-curve peak; and a negative result is indicated by the absence of an amplification curve or a characteristic melting-curve peak.

15. The method of claim 1, wherein the test sample is a fungal tissue sample extracted for molecular identification via PCR amplification of the target gene region, comprising the steps of:

(A15) preparing a tube containing a PCR solution by mixing 2 μL of a qPCR mix solution at a 5× concentration, 0.4 μL of a first primer solution at a 10 μM concentration, 0.4 μL of a second primer solution at a 10 μM concentration, 0.6 μL of a betaine solution at a 5 M concentration, 0.15 μL of dimethyl sulfoxide (DMSO), and 6.45 μL of ultrapure water; wherein when the target gene region is ITS, the first primer has the sequence set forth in SEQ ID NO. 101 and the second primer has the sequence set forth in SEQ ID NO. 102;

when the target gene region is nrSSU, the first primer has the sequence set forth in SEQ ID NO. 103 and the second primer has the sequence set forth in SEQ ID NO. 104;

when the target gene region is nrLSU, the first primer has the sequence set forth in SEQ ID NO. 105 and the second primer has the sequence set forth in SEQ ID NO. 106;

when the target gene region is tubulin, the first primer has the sequence set forth in SEQ ID NO. 107 and the second primer has the sequence set forth in SEQ ID NO. 108;

(B15) amplifying the test sample and reading the result by performing the following steps from (a15) to (c15):

(a15) immersing the test sample by dipping the dipstick containing DNA of the fungal tissue sample into the tube of step (A15) for 5 seconds, removing excess solution by touching the tube wall, then sealing the tube to obtain a sample-loaded reaction tube;

(b15) placing the sample-loaded reaction tube in a thermocycler and running the following program:

wherein, when the target gene regions are ITS and tubulin, the thermal cycling program comprises:

step 1: 95° C. for 5 minutes;

step 2: 35 cycles, each cycle comprising 94° C. for 15 seconds (denaturation), 57° C. for 30 seconds (annealing), and 72° C. for 60 seconds (extension); and step 3: 72° C. for 5 minutes;

wherein, when the target gene region is nrSSU, the thermal cycling program comprises:

step 1: 95° C. for 5 minutes;

step 2: 35 cycles, each cycle comprising 94° C. for 15 seconds (denaturation), 43° C. for 30 seconds (annealing), and 72° C. for 60 seconds (extension); and step 3: 72° C. for 5 minutes;

wherein, when the target gene region is nrLSU, the thermal cycling program comprises:

step 1: 95° C. for 5 minutes;

step 2: 35 cycles, each cycle comprising 94° C. for 15 seconds (denaturation), 55° C. for 30 seconds (annealing), and 72° C. for 60 seconds (extension); and step 3: 72° C. for 5 minutes;

(c15) analyzing the amplification products by agarose gel electrophoresis using a 1.5% agarose gel in 1×TAE buffer at 100 V for 45 minutes, staining with nucleic acid gel stain solution, and visualizing under UV illumination; wherein a positive result is indicated by the presence of a DNA band at the specific expected size for each gene region, including:

471-1100 base pairs for the ITS region;

1102 base pairs for the nrSSU region;

938 base pairs for the nrLSU region;

860 base pairs for the tubulin region;

a negative result is indicated by the absence of any DNA band.

16. The method of claim 1, wherein the test sample is a fungal tissue sample extracted to detect a target gene region by the real-time PCR, comprising the steps of:

(A16) preparing a tube containing a real-time PCR solution by mixing 2 μL of a qPCR mix solution at a 5× concentration, 0.4 μL of a first primer solution at a 10 μM concentration, 0.4 μL of a second primer solution at a 10 μM concentration, 0.6 μL of a betaine solution at a 5 M concentration, 0.15 μL of dimethyl sulfoxide (DMSO), and 6.45 μL of ultrapure water; wherein when the target gene region is ITS, the first primer has the sequence set forth in SEQ ID NO. 101 and the second primer has the sequence set forth in SEQ ID NO. 102;

when the target gene region is nrSSU, the first primer has the sequence set forth in SEQ ID NO. 103 and the second primer has the sequence set forth in SEQ ID NO. 104;

when the target gene region is nrLSU, the first primer has the sequence set forth in SEQ ID NO. 105 and the second primer has the sequence set forth in SEQ ID NO. 106;

when the target gene region is tubulin, the first primer has the sequence set forth in SEQ ID NO. 107 and the second primer has the sequence set forth in SEQ ID NO. 108;

(B16) amplifying the test sample and reading the result by performing the following steps from (a16) to (c16):

(a16) immersing the test sample by dipping the dipstick containing DNA of the fungal tissue sample into the tube of step (A16) for 5 seconds, removing excess solution by touching the tube wall, then sealing the tube to obtain a sample-loaded reaction tube;

(b16) placing the sample-loaded reaction tube in a real-time PCR instrument and running the following thermal program:

wherein, when the target gene regions are ITS and tubulin, the thermal cycling program comprises:

step 1: 95° C. for 5 minutes;

step 2: 35 cycles, each cycle comprising 94° C. for 15 seconds (denaturation), 57° C. for 30 seconds (annealing), and 72° C. for 60 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

wherein, when the target gene region is nrSSU, the thermal cycling program comprises:

step 1: 95° C. for 5 minutes;

step 2: 35 cycles, each cycle comprising 94° C. for 15 seconds (denaturation), 43° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

wherein, when the target gene region is nrLSU, the thermal cycling program comprises:

step 1: 95° C. for 5 minutes;

step 2: 35 cycles, each cycle comprising 94° C. for 15 seconds (denaturation), 55° C. for 30 seconds (annealing), and 72° C. for 60 seconds (extension);

step 3: 72° C. for 5 minutes;

step 4: performing a melting curve analysis by holding at 95° C. for 1 minute, then increasing from 70° C. to 95° C. at 0.2° C. every 2 seconds;

(c16) reading the result on the real-time PCR instrument, wherein a positive result is indicated by the appearance of an amplification curve and a characteristic melting-curve peak; and a negative result is indicated by the absence of an amplification curve or a characteristic melting-curve peak.

17. The method of claim 1, wherein the test sample is a swab sample containing human oral mucosal cells extracted to detect a beta actin gene by the PCR, comprising the steps of:

(A17) preparing a tube containing a PCR solution by mixing 2 μL of a qPCR mix solution at a 5× concentration, 0.4 μL of a beta F primer solution at a 10 μM concentration, 0.4 μL of a beta R primer solution at a 10 μM concentration, 0.6 μL of a betaine solution at a 5 M concentration, 0.15 μL of dimethyl sulfoxide (DMSO), and 6.45 μL of ultrapure water; wherein the beta F primer has the sequence set forth in SEQ ID NO. 109; and the beta R primer has the sequence set forth in SEQ ID NO. 110;

(B17) amplifying the test sample and reading the result by performing the following steps from (a17) to (c17):

(a17) immersing the test sample by dipping the dipstick containing DNA of the swab sample into the tube of step (A17) for 5 seconds, removing excess solution by touching the tube wall, then sealing the tube to obtain a sample-loaded reaction tube;

(b17) placing the sample-loaded reaction tube in a thermocycler and running the following program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes; and (c17) analyzing the amplification products by agarose gel electrophoresis using a 1.5% agarose gel in 1×TAE buffer at 100 V for 45 minutes, staining with nucleic acid gel stain solution, and visualizing under UV illumination; wherein a positive result is indicated by the presence of a DNA band at approximately 319 base pairs, and a negative result is indicated by the absence of a DNA band at approximately 319 base pairs.

18. The method of claim 1, wherein the test sample is a swab sample extracted to detect a beta actin gene by the real-time PCR, comprising the steps of:

(A18) preparing a tube containing a real-time PCR solution by mixing 2 μL of a qPCR mix solution at a 5× concentration, 0.4 μL of a beta F primer solution at a 10 μM concentration, 0.4 μL of a beta R primer solution at a 10 μM concentration, 0.6 μL of a betaine solution at a 5 M concentration, 0.15 μL of dimethyl sulfoxide (DMSO), and 6.45 μL of ultrapure water, wherein the beta F primer has the sequence set forth in SEQ ID NO. 109; and the beta R primer has the sequence set forth in SEQ ID NO. 110;

(B18) amplifying the test sample and reading the result by performing the following steps from (a18) to (c18):

(a18) immersing the test sample by dipping the dipstick containing DNA of the swab sample into the tube of step (A18) for 5 seconds, removing excess solution by touching the tube wall, then sealing the tube to obtain a sample-loaded reaction tube;

(b18) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 56° C. for 30 seconds (annealing), and 72° C. for 30 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c18) reading the result on the real-time PCR instrument, wherein a positive result is indicated by the appearance of an amplification curve and a characteristic melting-curve peak; and a negative result is indicated by the absence of an amplification curve or a characteristic melting-curve peak.

19. The method of claim 1, wherein the test sample is a plant tissue sample extracted to detect a CLO gene by the PCR, comprising the steps of:

(A19) preparing a tube containing a PCR solution by mixing 2 μL of a qPCR mix solution at a 5× concentration, 0.4 μL of a CLO-F primer solution at a 10 μM concentration, 0.4 μL of a CLO-R primer solution at a 10 μM concentration, 0.6 μL of a betaine solution at a 5 M concentration, 0.15 μL of dimethyl sulfoxide (DMSO), and 6.45 μL of ultrapure water; wherein the CLO-F primer has the sequence set forth in SEQ ID NO. 111; and the CLO-R primer has the sequence set forth in SEQ ID NO. 112;

(B19) amplifying the test sample and reading the result by performing the following steps from (a19) to (c19):

(a19) immersing the test sample by dipping the dipstick containing DNA of the plant tissue sample into the tube of step (A19) for 5 seconds, removing excess solution by touching the tube wall, then sealing the tube to obtain a sample-loaded reaction tube;

(b19) placing the sample-loaded reaction tube in a thermocycler and running the following program:

step 1: 95° C. for 5 minutes;

step 2: 35 cycles, each cycle comprising 94° C. for 15 seconds (denaturation), 60° C. for 30 seconds (annealing), and 72° C. for 60 seconds (extension);

step 3: 72° C. for 5 minutes; and (c19) analyzing the amplification products by agarose gel electrophoresis using a 1.5% agarose gel in 1×TAE buffer at 100 V for 45 minutes, staining with nucleic acid gel stain solution, and visualizing under UV illumination; wherein a positive result is indicated by the presence of a DNA band at approximately 422 base pairs, and a negative result is indicated by the absence of a DNA band at approximately 422 base pairs.

20. The method of claim 1, wherein the test sample is a plant tissue sample extracted to detect a CLO gene by the real-time PCR, comprising the steps of:

(A20) preparing a tube containing a real-time PCR solution by mixing 2 μL of a qPCR mix solution at a 5× concentration, 0.4 μL of a CLO-F primer solution at a 10 μM concentration, 0.4 μL of a CLO-R primer solution at a 10 μM concentration, 0.6 μL of a betaine solution at a 5 M concentration, 0.15 μL of dimethyl sulfoxide (DMSO), and 6.45 μL of ultrapure water, wherein the CLO-F primer has the sequence set forth in SEQ ID NO. 111; and the CLO-R primer has the sequence set forth in SEQ ID NO. 112;

(B20) amplifying the test sample and reading the result by performing the following steps from (a20) to (c20):

(a20) immersing the test sample by dipping the dipstick containing DNA of the plant tissue sample into the tube of step (A20) for 5 seconds, removing excess solution by touching the tube wall, then sealing the tube to obtain a sample-loaded reaction tube;

(b20) placing the sample-loaded reaction tube in a real-time PCR instrument and running the following thermal program:

step 1: 95° C. for 5 minutes;

step 2: 35 cycles, each cycle comprising 94° C. for 15 seconds (denaturation), 60° C. for 30 seconds (annealing), and 72° C. for 60 seconds (extension);

step 3: 72° C. for 5 minutes;

step 4: performing a melting curve analysis by holding at 95° C. for 1 minute, then increasing from 70° C. to 95° C. at 0.2° C. every 2 seconds; and (c20) reading the result on the real-time PCR instrument, wherein a positive result is indicated by the appearance of an amplification curve and a characteristic melting-curve peak; and a negative result is indicated by the absence of an amplification curve or a characteristic melting-curve peak.

* * * * *